US008420326B2

(12) United States Patent
Nishikawa et al.

(10) Patent No.: US 8,420,326 B2
(45) Date of Patent: Apr. 16, 2013

(54) METHOD OF EVALUATING PERFORMANCE OF ACTIVATION GAS DEACTIVATING ANTIGENIC SUBSTANCE AND APPARATUS FOR GENERATING PROCESSED ANTIGENIC SUBSTANCE USED AS EVALUATION SAMPLE OF THE EVALUATING METHOD

(75) Inventors: Kazuo Nishikawa, Higashiosaka (JP); Hideo Nojima, Nara (JP); Tetsuya Yoneda, Nabari (JP); Kazuhisa Ono, Higashihiroshima (JP); Seiko Shigeta, Hiroshima (JP); Masatoshi Oshita, Fukuchiyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 1435 days.

(21) Appl. No.: 10/545,239

(22) PCT Filed: Feb. 13, 2004

(86) PCT No.: PCT/JP2004/001602
§ 371 (c)(1), (2), (4) Date: Apr. 10, 2007

(87) PCT Pub. No.: WO2004/074832
PCT Pub. Date: Sep. 2, 2004

(65) Prior Publication Data

US 2007/0264192 A1 Nov. 15, 2007

(30) Foreign Application Priority Data

Feb. 18, 2003 (JP) ................................ 2003-040352
Sep. 1, 2003 (JP) ................................ 2003-308735

(51) Int. Cl.
*G01N 33/53* (2006.01)

(52) U.S. Cl.
USPC ............................ 435/7.1; 436/501; 436/518

(58) Field of Classification Search ........................ None
See application file for complete search history.

(56) References Cited

U.S. PATENT DOCUMENTS

| | | | | |
|---|---|---|---|---|
| 4,060,597 | A * | 11/1977 | Sato et al. | 436/534 |
| 4,632,980 | A | 12/1986 | Zee et al. | |
| 5,491,068 | A * | 2/1996 | Benjamin et al. | 435/7.32 |
| 5,665,351 | A * | 9/1997 | Nair et al. | 424/93.47 |
| 6,303,152 | B1 | 10/2001 | Kief | |
| 6,613,358 | B2 * | 9/2003 | Randolph et al. | 424/489 |
| 6,736,133 | B2 * | 5/2004 | Bachinski et al. | 126/521 |
| 7,040,101 | B2 * | 5/2006 | Takeda et al. | 62/78 |
| 2005/0168907 | A1 * | 8/2005 | Sekoguchi et al. | 361/230 |

FOREIGN PATENT DOCUMENTS

| | | | |
|---|---|---|---|
| CA | 2 409 000 | A1 | 11/2001 |
| DE | 198 29 091 | A1 | 1/2000 |
| EP | 0 535 612 | A1 | 4/1993 |
| JP | 62-000021 | A | 1/1987 |
| JP | 63-188391 | A | 8/1988 |
| JP | 5-087805 | A | 4/1993 |
| JP | 6-154298 | A | 6/1994 |
| JP | 07-000807 | A | 1/1995 |
| JP | 8-173843 | A | 7/1996 |
| JP | 2000-111106 | A | 4/2000 |
| JP | 2002-181371 | A | 6/2002 |
| JP | 2003-180865 | A | 7/2003 |
| WO | WO 02/17978 | * | 3/2002 |

OTHER PUBLICATIONS

Williams, Intramural spread of bacteria and viruses in human populations, Annual Review of Microbiology, vol. 14, 1960, pp. 43-64.*

* cited by examiner

*Primary Examiner* — Gary W Counts
(74) *Attorney, Agent, or Firm* — Birch, Stewart, Kolasch & Birch, LLP

(57) ABSTRACT

A method of evaluating performance of an activation gas deactivating an antigenic substance including the steps of causing the antigenic substance and the activation gas to react with each other, to obtain a processed antigenic substance, and causing an antibody against the antigenic substance with the processed antigenic substance to measure binding activity of the processed antigenic substance with the antibody is provided, whereby an evaluation method that can accurately and easily evaluate performance of an activation gas deactivating an antigenic substance is provided.

7 Claims, 19 Drawing Sheets

METHOD OF EVALUATING PERFORMANCE OF ACTIVATION GAS DEACTIVATING ANTIGENIC SUBSTANCE AND APPARATUS FOR GENERATING PROCESSED ANTIGENIC SUBSTANCE USED AS EVALUATION SAMPLE OF THE EVALUATING METHOD

TECHNICAL FIELD

The present invention relates to a method of evaluating performance of an activation gas activating an antigenic substance. More specifically, the present invention relates to a method of evaluating performance of an activation gas, deactivating an antigenic substance by a reaction between the antigenic substance that causes an allergic reaction in mammal with the activation gas.

Further, the present invention relates to an apparatus for generating processed antigenic substance processed by the activation gas. More specifically, the present invention relates to an apparatus having a container, for generating processed antigenic substance used as evaluation sample for evaluating performance of an activation gas deactivating an antigenic substance.

BACKGROUND ART

Recently, along with change in residential environment, there has been an increasing demand to remove harmful airborne substances such as pollen, mite, mite waste, house dust and the like that may cause allergic disease such as hey fever, asthma, cutaneous atopy, conjunctivitis and the like of mammals including human, to realize more healthy and comfortable life.

In order to meet such a demand, it is effective to remove an antigenic substance (allergen) as the cause of allergic diseases described above, and air conditioning apparatuses with various filters and dust collectors have been developed (see, for example, Japanese Patent Laying-Open No. 8-173843).

These air conditioning apparatuses are of the type that absorb or filter harmful airborne substance by sucking in air in the space through a filter. Therefore, such apparatuses inherently necessitate maintenance such as filter exchange for use over a long period of time, and in addition, satisfactory performance can not always be attained because of insufficient properties of the filter.

In such type of air conditioning apparatuses, when collection of pollen is intended, for example, the pollen having antigenic protein as the cause of hey fever is physically trapped and remains on a collection filter. The physically trapped pollen easily comes off from the collection filter, and therefore, there is a problem that at the time of starting or stopping operation, or at the time of filter exchange, the trapped pollen might possibly be scattered again. Further, even if the pollen itself can be trapped by the collection filter, the antigenic protein having smaller grain size may pass through the collection filter, and therefore, the antigenic substance cannot be eradicated.

A pollen processing apparatus that denatures the antigenic substance by heat treatment, in addition to various filters, has also been developed (see, for example, Japanese Patent Laying-Open No. 7-807).

Such an air conditioning apparatus, however, consumes much energy for the heat treatment, resulting in much increased electricity bill at home and environmentally negative influence. If such an air conditioning apparatus is used in the summer season or hot region, room temperature would considerably increase and the user would feel uncomfortable. Therefore, such a mechanism cannot be used incorporated in a cooler.

An apparatus that deactivates cedar hey fever antigen by ultraviolet radiation, in addition to various filters, has also been developed (see, for example, Japanese Patent Laying-Open No. 6-154298).

Such an air conditioning apparatus, however, consumes much energy for the ultraviolet radiation, resulting in much increased electricity bill at home and environmentally negative influence. Further, according to the reference above, in order to lower the antibody value of cedar pollen sample, ultraviolet irradiation with the intensity of at least 1.3 $mW/cm^2$ for at least 50 seconds is necessary. Namely, the ability to deactivate antigen of cedar hey fever is low, and hence, this cannot be considered a practical technique.

An air purifier generating ozone by ultraviolet irradiation, in addition to various filters, has also been developed (see, for example, Japanese Patent Laying-Open No. 2000-111106).

Such an air conditioning apparatus, however, consumes much energy for the ultraviolet radiation, resulting in much increased electricity bill at home and environmentally negative influence. Further, ozone emitted to the atmosphere may in some cases affect life of mammals including humans.

Antigenic substance must be processed differently type by type as the antigenic substance cause allergic reaction that differ one person to another, and none of the air conditioning apparatuses above can solve this problem. Further, effect of various removing means or deactivating means differ type by type of the antigenic substance, and this problem is not solved, either.

In view of the foregoing, an object of the present invention is to provide a method of evaluating performance of various activation gases deactivating various antigenic substances, which method is necessary in realizing an air conditioning apparatus that can efficiently remove and/or deactivate antigenic substance by an activation gas of the type and/or amount matching the type and/or amount of the antigenic substance, to which reaction differ one person to another.

Another object of the present invention is to provide an apparatus for generating a processed antigenic substance that can generate the antigenic substance processed by the activation gas to be used as evaluation sample, in uniform quality and in a simple manner.

DISCLOSURE OF THE INVENTION

In order to solve the above-described problems, the inventors made trial and error to establish a method of evaluation of performance of the activation gas deactivating an antigenic substance.

As a result, the inventors have found that a processed antigenic substance having uniform quality, processed by the activation gas can be obtained in a simple manner, by diffusing an antigenic substance in a container and causing reaction of the diffused solution including the antigenic substance with the activation gas while the solution is floating in the container.

The inventors have also found that using the processed antigenic substance, the performance of activation gas deactivating antigenic substance can be evaluated accurately in a simple manner.

Specifically, the present invention provides a method of evaluating performance of an activation gas deactivating an antigenic substance, including the steps of causing the antigenic substance and the activation gas to react with each other, to obtain a processed antigenic substance; and causing an antibody against the antigenic substance to react with the processed antigenic substance to measure binding activity of the processed antigenic substance with the antibody.

Alternatively, the present invention provides a method of evaluating performance of an activation gas deactivating an antigenic substance, including the steps of causing the antigenic substance and the activation gas to react with each other, to obtain a processed antigenic substance; causing an antibody against the antigenic substance to react with the processed antigenic substance to measure binding activity of the processed antigenic substance with the antibody; and comparing the binding activity of the processed antigenic substance to binding activity of the antigenic substance with the antibody.

Here, preferably, the step of obtaining the processed antigenic substance includes the step of causing the antigenic substance floating in the air and the activation gas to react with each other.

Further, desirably, the step of causing reaction includes the steps of: dispersing a solution containing the antigenic substance in a container, causing the dispersed solution containing the antigenic substance to float in the air, and introducing the activation gas into the container.

Preferably, the step of obtaining the processed antigenic substance includes the step of causing the antigenic substance to float in the air, by vibrating and/or shocking the antigenic substance.

Further, preferably, the step of causing floating includes the steps of: placing the antigenic substance on a flexible sample table; and vibrating and/or shocking the sample table.

Here, desirably, the step of causing floating includes the steps of: placing the antigenic substance on a flexible sample table formed of at least one selected from the group consisting of a futon, a blanket, a cushion, a pillow, a mat, a sponge, cloth, paper and styrene foam; and vibrating and/or shocking the sample table by flapping and/or shaking the sample table.

Further, preferably, the step of obtaining the processed antigenic substance includes the step of causing the antigenic substance to react with a gas containing at least one selected from the group consisting of a gas containing positive ions, a gas containing negative ions, a gas containing radicals, an ozone gas, and a nitric acid gas.

Further, preferably, the step of obtaining the processed antigenic substance includes the step of causing at least one selected from the group consisting of an antigenic substance included in cedar pollen and/or mite dust, cedar pollen and mite dust to react with the activation gas, to obtain the processed antigenic substance.

Desirably, the step of measurement includes the step of causing an antibody against the antigenic substance and the processed antigenic substance to react with each other by ELISA method and/or ELISA inhibition method, to measure binding activity of the processed antigenic substance with the antibody.

Preferably, the step of measurement includes the step of causing the antibody and the processed antigenic substance to react with each other by intradermal test and/or conjectival test on an animal other than human, having a cell producing an antibody against the antigenic substance, to measure binding activity of the processed antigenic substance with the antibody.

The present invention provides an apparatus for generating a processed antigenic substance to be used as an evaluation sample for evaluating performance of an activation gas deactivating an antigenic substance, including: a container; means for dispersing an antigenic substance into the container; and means for generating or introducing the activation gas in or into the container.

The present invention also provides an apparatus for generating a processed antigenic substance to be used as an evaluation sample for evaluating performance of an activation gas deactivating an antigenic substance, including: a container; means for enclosing an antigenic substance in the container; and means for generating or introducing the activation gas in or into the container.

In any of the apparatuses for generating a processed antigenic substance in accordance with the present invention described above, preferably, the container partially or fully includes a transparent material.

BEST MODES FOR CARRYING OUT THE INVENTION

Figure 1:
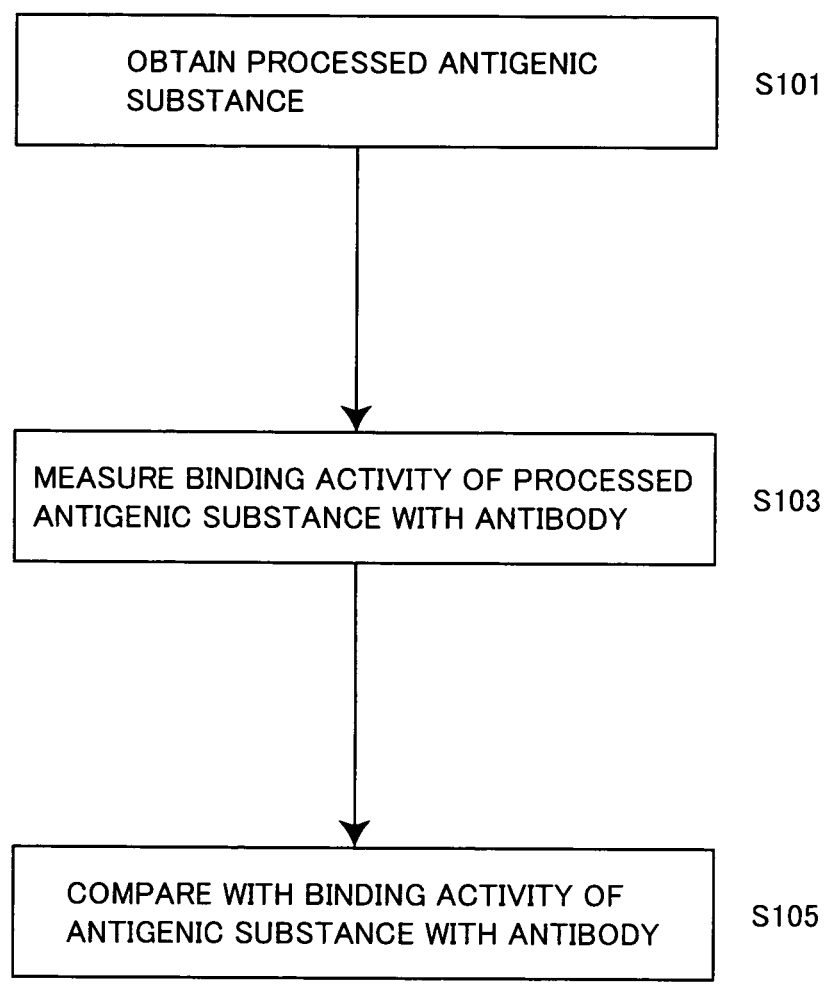
FIG. 1 is a flow chart schematically showing a method of evaluating performance of an activation gas deactivating an antigenic substance in accordance with the present invention.

In the following, the present invention will be described in grater detail with reference to embodiments.
<Antigenic Substance>

In the present specification, the antigenic substance refers to a substance included in pollen of cedar, cypress or ragweed, in living organism such as mite, waste of living organism such as mite waste or in air-borne substance at home such as house-dust that acts on a living body of mammals including human to cause an allergic reaction as one type of antigen-antibody reaction, inducing allergic disease.

Such an antigenic substance typically consists of protein or glycoprotein. In the present specification, its shape or size is not specifically limited, and the protein or glycoprotein itself as molecules, collected particles thereof, or antibody-reactive portion (also referred to as an antigenic determinant or epitope) as a part of the molecular body may be included.

The antigenic substance may be cedar pollen itself or antigenic substance included in cedar pollen (cedar antigenic substance). Alternatively, the antigenic substance may be mite dust itself or antigenic substance included in mite dust (mite antigenic substance).

Consider the antigenic substance as a cause of cedar hey fever. The antigenic substance includes Cry j 1 protein and Cry j 2 protein known as the causative agents of cedar hey fever, epitope of Cry j 1 protein and Cry j 2 protein, particles in cedar pollen (referred to as Ubish body or orbicle) including large amount of Cry j 1 protein and Cry j 2 protein, as well as cedar pollen itself.

The mite antigenic substance is included in the body of mite. In general life environment, however, the antigenic substance not in mite itself but in mite dust causes problems. Here, mite dust refers to particles including mite itself, dead mite, part of mite body, mite bait, body waste, shell or egg of mite. In the present invention, the antigenic substance includes such mite dust.
<Antibody-Reactive Portion>

In the present specification, the antibody-reactive portion refers to a specific portion included in the antigenic substance that combines with the antibody. If the antibody-reactive portion of the antigenic substance were denatured or destroyed (decomposed), the antigenic substance could not combine with the antibody, and therefore, allergic reaction can be suppressed.
<Activation Gas>

In the present specification, the activation gas means a gas that causes some chemical reaction and/or physical reaction on the antigenic substance. Specific example of the activation gas is not particularly limited, an it may include a gas containing positive ions, a gas containing negative ions, a gas containing both positive and negative ions, a gas containing ozone, a gas containing nitric acid gas, and a gas containing radicals. There may possibly be gases of various components that can serve as the activation gas against the antigenic substance, and such activation gas can be found using the method of evaluating performance of the activation gas deactivating the antigenic substance of the present invention, as will be described later.

The fact that the gas containing both positive and negative ions acts as an activation gas against the antigenic substance and has a function of deactivating the antigenic substance, as will be described later, has not been conventionally known, and it is a phenomenon found for the first time by the inventors of the present invention using the method of evaluating the performance of the activation gas deactivating the antigenic substance in accordance with the present invention.
<Deactivation of Antigenic Substance>

In the present specification, deactivation of an antigenic substance means elimination or decrease of activity of antigenic substance as the antigenic substance. Specifically, it means elimination or decrease of the ability of antigenic substance to react against the antibody.

Here, the inventors understand that the mechanism of deactivation of the antigenic substance by the activation gas is that the activation gas attacks protein forming the antigenic substance, particularly the antibody-reactive portion, so that the protein is denatured or destroyed (decomposed).

Further, as will be described later, a gas containing both positive and negative ions acts as activation gas against the antigenic substance, and has a function of deactivating the antigenic substance, which phenomenon has been found for the first time by the inventors using the method of evaluating the performance of activation gas deactivating the antigenic substance, in accordance with the present invention. The deactivating function is attained by causing the positive and negative ions act against the antigenic substance.

Though it has not been known conventionally, according to the findings of the inventors, when a gas containing both positive and negative ions is used, remarkably high deactivating function is exhibited than when a gas containing positive ions only or negative ions only is used. According to the findings of the inventors, when the gas having positive and negative ions exist together is used, active substance is generated through a chemical reaction as will be described later, and the active substance attacks the protein forming the antigenic substance, particularly the antibody-reactive portion thereof, so that the protein is denatured or destroyed (decomposed), whereby the antigenic substance is deactivated.

Specifically, in the present specification, deactivation of the antigenic substance is, in more detailed definition, to eliminate the antigenic substance, as well as to reduce the amount of antigenic substance per unit volume of an atmospheric gas, and to lower reactivity of the antibody-reactive portion of the antigenic substance and the antibody, by denaturing or destroying (decomposing) the antigenic substance, as described above.

There are various methods of measuring (or defining) the ratio of deactivation (or remaining activity) of the antigenic substance, and an appropriate method may be selected in accordance with the type of the antigenic substance and the type of the activation gas. Though not limiting, ELISA inhibition method may be used as the method of measurement. According to this method, when a concentration that represents 50% inhibition of the antigenic substance processed with the activation gas is measured, and the 50% inhibition concentration is at least five times the 50% inhibition concentration of the antigenic substance not processed with the activation gas, then, the remaining activity is 20% (that is, the ratio of deactivation is 80%).

How high a ratio of deactivation should be attained to determine that an activation gas has an ability to deactivate an antigenic substance depends on the type of the activation gas and the type of antigenic substance, and it may be determined using an appropriate threshold value. Though not specifically limiting, a gas containing positive and negative ions may be used as the activation gas, and an antigenic substance derived from cedar pollen can be used.

<Method of Evaluating Performance of Activation Gas Deactivating Antigenic Substance>

FIG. 1 is a flow chart schematically representing a method of evaluating the performance of an activation gas deactivating an antigenic substance, in accordance with the present invention.

The present invention provides a method of evaluating performance of an activation gas deactivating an antigenic substance, basically including the steps of causing the antigenic substance and the activation gas to react with each other, to obtain a processed antigenic substance (S101); and causing an antibody against the antigenic substance to react with the processed antigenic substance to measure binding activity of the processed antigenic substance with the antibody (S103). Preferably, the method of evaluating performance of an activation gas deactivating an antigenic substance of the present invention may further include, as can be seen from the flow chart of FIG. 1, following the above-described steps of causing the antigenic substance and the activation gas to react with each other, to obtain a processed antigenic substance (S101) and causing an antibody against the antigenic substance to react with the processed antigenic substance to measure binding activity of the processed antigenic substance with the antibody (S103), the step of comparing the binding activity of the processed antigenic substance to binding activity of the antigenic substance with the antibody (S105).

As the method of evaluation employing a comparison with a controlled sample is used, the performance of activation gas deactivating the antigenic substance can advantageously be evaluated accurately in a simple manner, and quantitatively. Here, if the binding activity between the antibody and the antigenic substance (it is generally expected that antigenic substance not processed with activation gas is used in most cases) is to be compared, a measurement made beforehand, or a measurement made every time evaluation is to be done in accordance with the present invention may be used as the binding activity of the antigenic substance against the antibody. From the viewpoint of more accurate result of evaluation, a measurement made at every evaluation is preferred. In order to obtain the result of evaluation quickly in a simple manner, use of a measurement made beforehand is preferred.

Preferably, the step of obtaining the processed antigenic substance includes the step of causing the antigenic substance floating in the air and the activation gas to react with each other.

As the activation gas is caused to react against the antigenic substance floating in the air, the antigenic substance and the activation gas can react in a uniform state, and by adjusting the time of floating of the antigenic substance, the reaction time between the antigenic substance and the activation gas can easily be adjusted. The antigenic substance may be lifted up to float in the air, by stirring, or causing the atmospheric gas containing the activation gas to flow. Alternatively, the antigenic substance may be caused to fall down for a prescribed distance to float in the air.

Further, desirably, the step of causing reaction includes the steps of dispersing the antigenic substance in the container, causing the dispersed solution containing the antigenic substance to float in the air, and introducing the activation gas into the container.

In this manner, as the solution containing the antigenic substance is dispersed in the container unintended diffusion of the antigenic substance can be prevented, and the concentration of the antigenic substance in the container can advantageously be kept in a prescribed range. Here, the container is preferably a sealed container, though a semi-sealed one having an opening may be used.

Further, as the solution containing the antigenic substance dispersed in this manner floats in the container, unintended diffusion of the antigenic substance can be prevented, and the concentration of the antigenic substance in the container can advantageously be kept in a prescribed range, even when the atmospheric gas containing the activation gas is stirred or caused to flow to lift up the antigenic substance.

Further, as the activation gas is introduced to the container in this manner, unintended diffusion of the activation gas can be prevented, and therefore, it becomes possible to cause uniform reaction between the activation gas having its concentration kept in a prescribed range and the antigenic substance, in the container in which the concentration of the antigenic substance is kept in a prescribed range.

Here, the antigenic substance is contained in the solution, and therefore, when the solution containing the antigenic substance is to be dispersed in the container, spraying with a nebulizer is preferred. The solution can be sprayed as minute and uniform particles, and hence, reaction between the antigenic substance and the activation gas can be made more uniform.

Further, in the method of evaluating performance of an activation gas deactivating an antigenic substance in accordance with the present invention, the step of obtaining the processed antigenic substance preferably includes the step of causing the antigenic substance to float in the air, by vibrating and/or shocking the antigenic substance. The step of causing floating includes the steps of placing the antigenic substance on a flexible sample table, and vibrating and/or shocking the sample table. Here, the flexible sample table is preferably formed of at least one selected from the group consisting of a futon, a blanket, a cushion, a pillow, a mat, a sponge, cloth, paper and styrene foam. Preferably, in the step of vibrating and/or shocking the sample table, the sample table is vibrated and/or shocked by flapping and/or shaking the sample table.

Further, preferably, the step of obtaining the processed antigenic substance includes the step of causing the antigenic substance to react with a gas containing at least one selected from the group consisting of a gas containing positive ions, a gas containing negative ions, a gas containing radicals, an ozone gas, and a nitric acid gas. Particularly, the step of obtaining the processed antigenic substance preferably is a step of causing a reaction between the antigenic substance and a gas containing both positive and negative ions.

The gas containing both positive and negative ions is preferred as it has been found for the first time by the inventors that it has the function of deactivating an antigenic substance derived from cedar pollen and it is expected to have a function of deactivating other antigenic substances, as will be described later. Further, performance of deactivating an antigenic substance of ozone gas, nitric acid gas, and a gas containing radicals can be evaluated by the method of evaluation described in the specification, as these are gaseous substances.

Desirably, the step of measurement includes the step of causing an antibody against the antigenic substance and the processed antigenic substance to react with each other by ELISA method and/or ELISA inhibition method, to measure binding activity of the processed antigenic substance with the antibody.

As described above, using the ELISA method and/or ELISA inhibition method, it is possible to accurately and easily measure binding activity of processed antigenic substance with the antibody.

By way of example, when a concentration indicating 50% inhibition of the antigenic substance processed with the activation gas is measured using the ELISA inhibition method, the 50% inhibition concentration may be compared with the 50% inhibition concentration of the antigenic substance not processed with the activation gas, as described above. In that case, when the 50% inhibition concentration is five times, the remaining activity is 20% (that is, the ratio of deactivation is 80%).

Preferably, the step of measurement includes the step of causing the antibody and the processed antigenic substance to react with each other by intradermal test and/or conjectival test on an animal other than human, having a cell producing an antibody against the antigenic substance, to measure binding activity of the processed antigenic substance with the antibody.

In this manner, by the intradermal test and/or conjuctival test on an animal other than human having a cell that produces an antibody against the antigenic substance, the binding activity of the processed antigenic substance with the antibody can advantageously be measured in a condition closer to a living human body. In the examples described below, human intradermal test and conjectival test were preformed. It is a technical common sense in the field of medical science, pharmaceutical science, agricultural science, biology, biochemistry and molecular biology that any living-body experiment that can be performed on human can more readily be performed on mammals other than human, such as mouse and rat.

<Apparatus for Generating Processed Antigenic Substance>

The present invention provides an apparatus for generating a processed antigenic substance to be used as an evaluation sample for evaluating performance of an activation gas deactivating an antigenic substance, including: a container; means for dispersing an antigenic substance into the container; and means for generating or introducing the activation gas in or into the container. Further, the apparatus for generating a processed antigenic substance may be an apparatus for generating a processed antigenic substance to be used as an evaluation sample for evaluating performance of an activation gas deactivating an antigenic substance, including: a container; means for enclosing an antigenic substance in the container; and means for generating or introducing the activation gas in or into the container.

By using such an apparatus, it becomes possible to cause reaction between the activation gas and the antigenic substance in a uniform state in a simple manner, and thus, a processed antigenic substance of high quality that can suitably be used as the evaluation sample for evaluating performance of an activation gas deactivating the antigenic substance can be generated. Preferably, the apparatus for generating the processed antigenic substance of the present invention may further include means for causing the antigenic substance to float in the container. By the container, diffusion of the activation gas and the antigenic substance is prevented. Therefore, even when the antigenic substance is lifted up to float in the container by stirring or causing the atmospheric gas to flow, concentrations of the antigenic substance and the activation gas can be kept in a prescribed range.

Here, preferably, the container partially or fully includes a transparent material.

As the container is partially or fully transparent, the state of antigenic substance floating in the container and the like can be visually monitored, and therefore, adjustment of reaction condition between the antigenic substance and the activation gas becomes easier.

Figure 2:
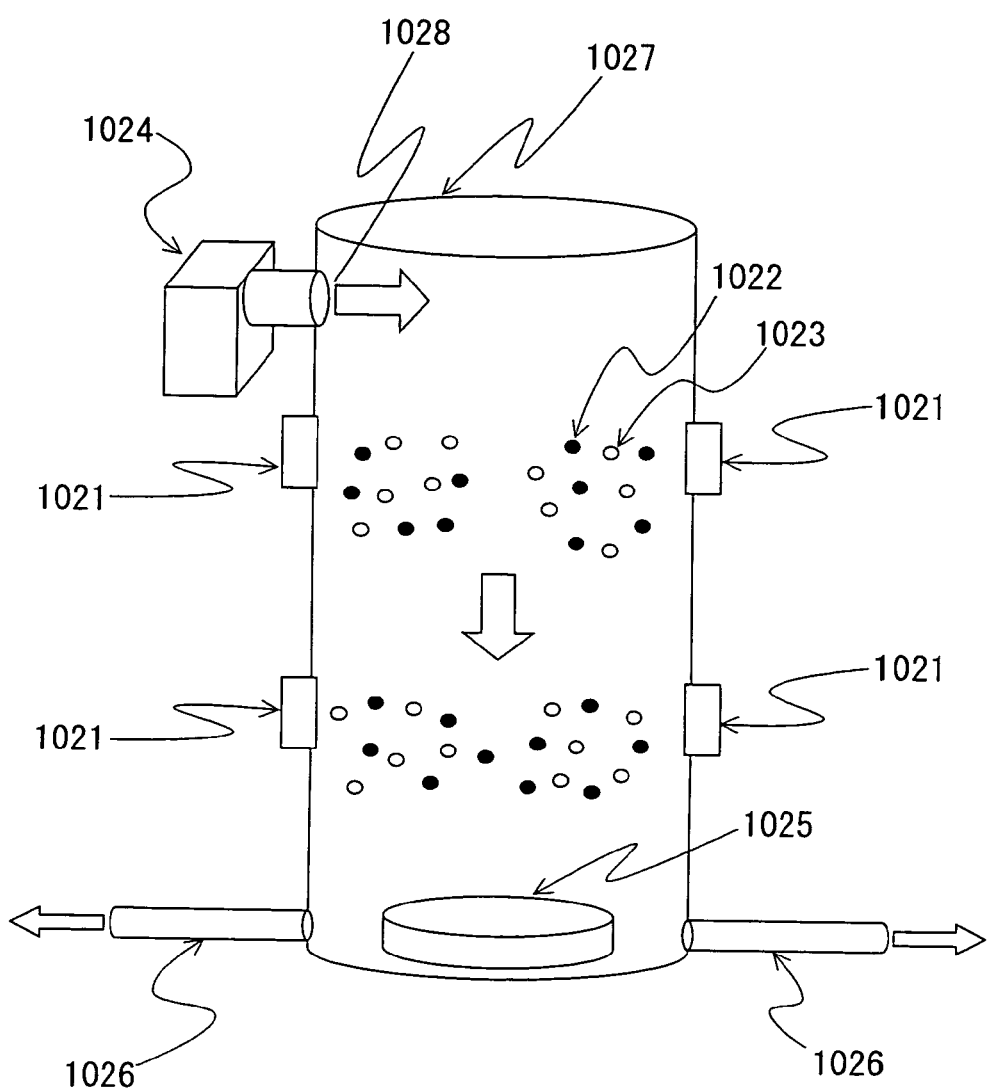
FIGS. 2 to 6 schematically show examples of apparatuses for generating a processed antigenic substance to be used as an evaluation sample for evaluating performance of an activation gas deactivating an antigenic substance in accordance with the present invention.

FIG. 2 schematically shows an example of the apparatus for generating the processed antigenic substance to be used as an evaluation sample for evaluating performance of an activation gas deactivating the antigenic substance in accordance with the present invention.

The apparatus shown in FIG. 2 includes, as the container, a semi-sealed cylindrical container 1027. As means for dispersing the antigenic substance, it includes a neblizer 1024 and an inlet 1028. As means for causing the antigenic substance to float in the container, semi-sealed cylindrical container 1027 is provided, as it has a prescribed height and hence, the antigenic substance necessarily floats therein. As means for introducing a gas containing both positive ions 1022 and negative ions 1023 as the activation gas into the container, an ion generating device 1021 is provided.

In addition, the apparatus shown in FIG. 2 includes a recovery vessel 1025 for recovering the antigenic substance processed with the activation gas, and an exhaustion outlet 1026 for evacuating the atmospheric gas including the activation gas.

Figure 3:
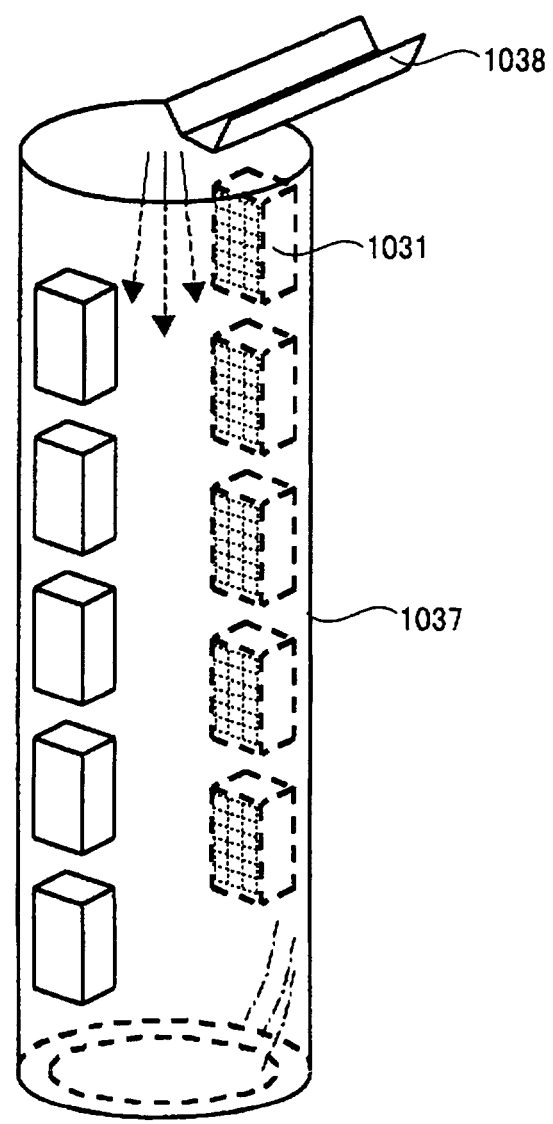

FIG. 3 schematically shows another example of the apparatus for generating a processed antigenic substance to be used as an evaluation sample for evaluating performance of an activation gas deactivating an antigenic substance in accordance with the present invention.

The apparatus shown in FIG. 3 includes, as a container, a semi-sealed cylindrical container 1037. As means for dispersing the antigenic substance, it includes an inlet 1038. Further, as means for causing the antigenic substance to float in the container, semi-sealed cylindrical container 1037 is provided, as it has a prescribed height and hence, the antigenic substance necessarily floats therein. As means for introducing a gas containing both positive and negative ions as the activation gas into the container, an ion generating device 1031 is provided.

Figure 4:
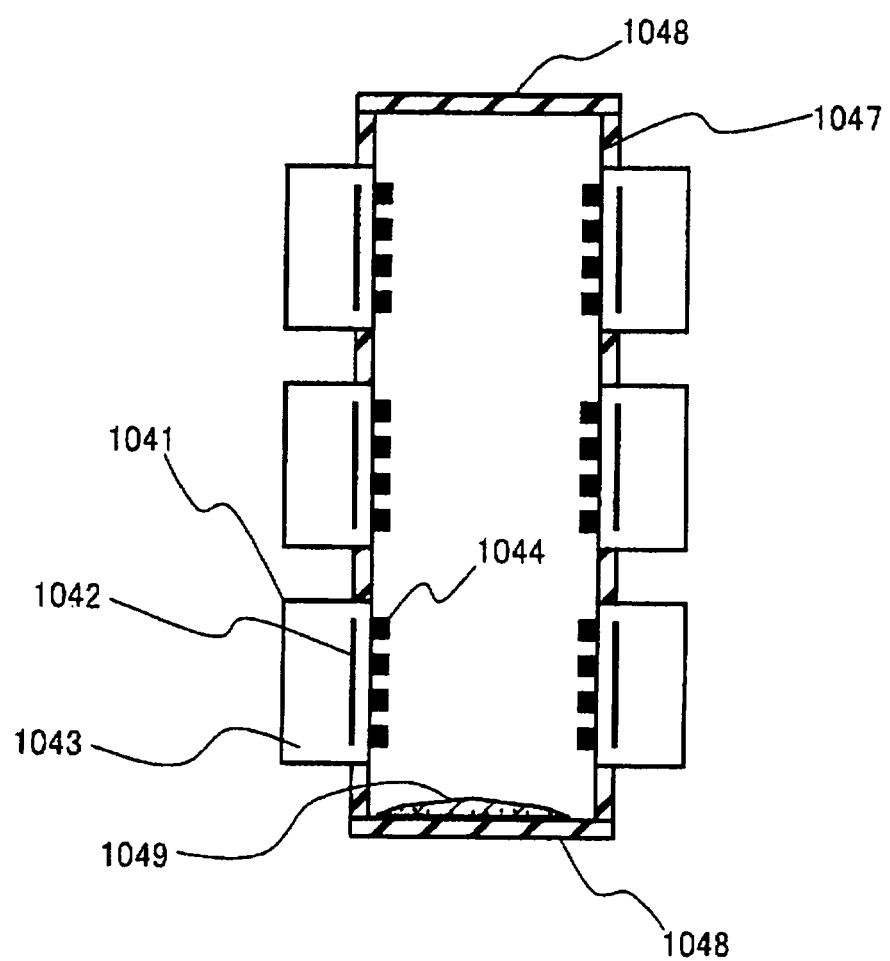

FIG. 4 schematically shows a further example of the apparatus for generating a processed antigenic substance to be used as an evaluation sample for evaluating performance of an activation gas deactivating an antigenic substance in accordance with the present invention.

The apparatus shown in FIG. 4 includes, as a container, a semi-sealed cylindrical container 1047. As means for dispersing the antigenic substance, it includes a lid 1048 that can be opened/closed. Further, as means for causing the antigenic substance to float in the container, semi-sealed cylindrical container 1047 is provided, as it has a prescribed height and hence, the antigenic substance necessarily floats therein when it is erected in the longitudinal direction or turned over repeatedly. Further, as means for introducing a gas containing both positive and negative ions as the activation gas into the container, an ion generating device 1041 is provided.

In addition, the apparatus of FIG. 4 is shown to include an antigenic substance 1049, a voltage applying electrode 1042, a dielectric 1043 and a ground electrode 1044.

Figure 5:
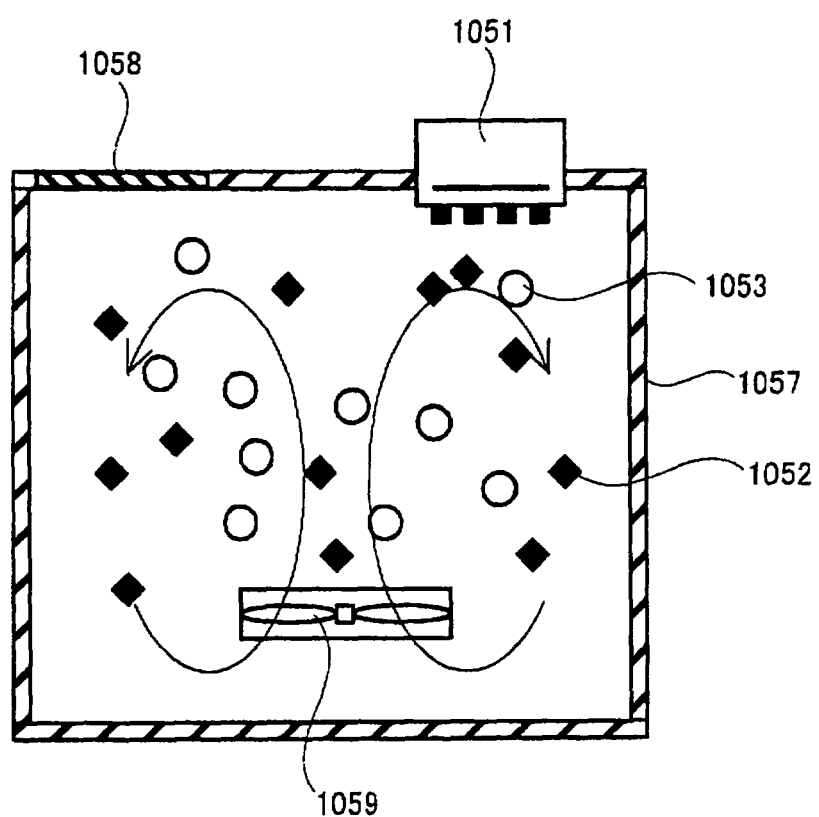

FIG. 5 schematically shows a further example of the apparatus for generating a processed antigenic substance to be used as an evaluation sample for evaluating performance of an activation gas deactivating an antigenic substance in accordance with the present invention.

The apparatus shown in FIG. 5 includes, as a container, a semi-sealed cylindrical container 1057. As means for dispersing the antigenic substance, it includes a lid 1058 that can be opened/closed. Further, as means for causing the antigenic substance to float in the container, a fan 1059 is provided.

Further, as means for introducing a gas containing both, positive and negative ions as the activation gas into the container, an ion generating device 1051 is provided.

Figure 6:
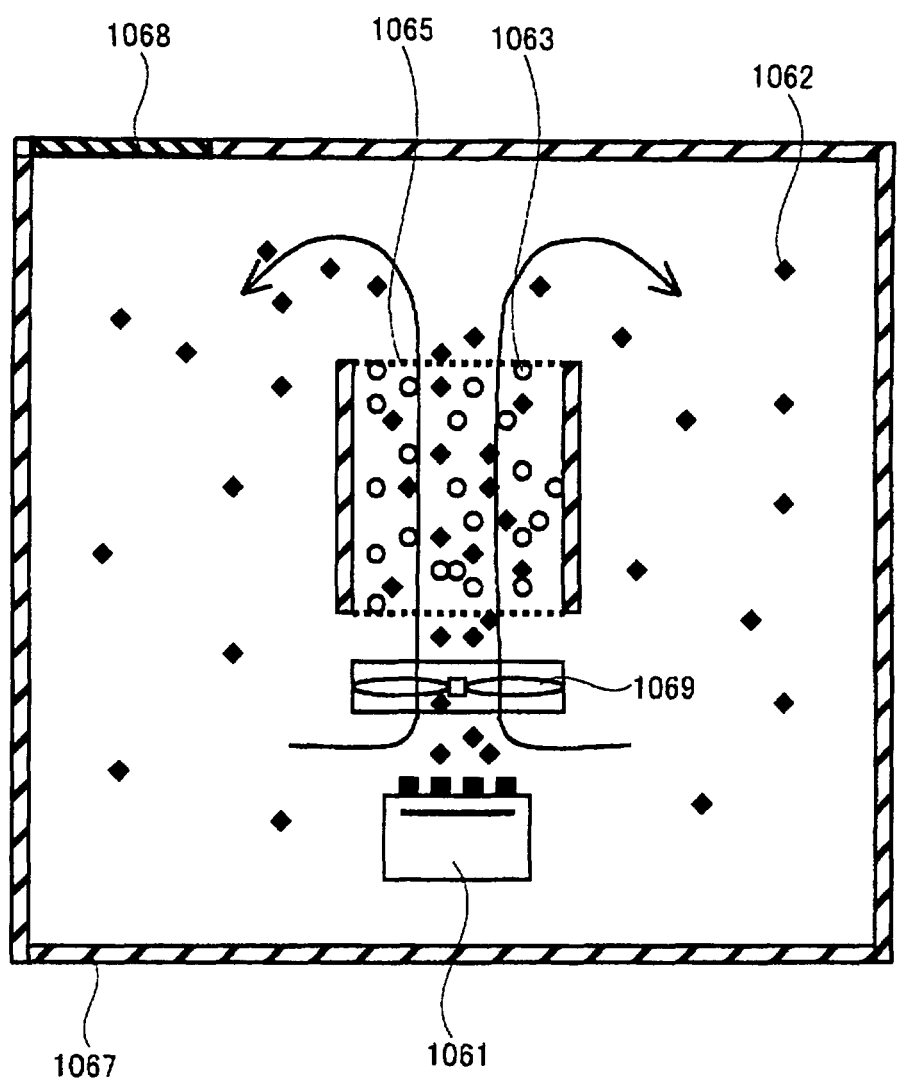

FIG. 6 schematically shows a still further example of the apparatus for generating a processed antigenic substance to be used as an evaluation sample for evaluating performance of an activation gas deactivating an antigenic substance in accordance with the present invention.

The apparatus shown in FIG. 6 includes, as a container, a semi-sealed cylindrical container 1067. As means for dispersing the antigenic substance, it includes a lid 1068 that can be opened/closed. Further, as means for causing the antigenic substance to float in the container, a fan 1069 and a filter 1065 that pass the activation gas but not the antigenic substance are provided. Further, as means for introducing a gas containing both positive and negative ions as the activation gas into the container, an ion generating device 1061 is provided.

<Ion Generating Device>

The ion generating device to be used in the apparatus for generating a processed antigenic substance to be used as an evaluation sample for evaluating performance of an activation gas deactivating an antigenic substance in accordance with the present invention preferably generates positive and negative ions, and possibly, by the electric shock as will be described later, it can directly deactivate allergic reaction of the antigenic substance.

The position of mounting such an ion generating device is not particularly limited. However, generally, it is preferably mounted in an air passage of the apparatus for deactivating the antigenic substance. The positive and negative ions generated by the ion generating device disappear in a short period of time, and therefore, the position is determined to efficiently diffuse the positive and negative ions in the air. One, two or more ion generating devices may be mounted.

A conventionally known ion generating device for generating positive and negative ions by a discharge mechanism is used as the ion generating device. Particularly, a device that can emit positive and negative ions to the air to attain the concentration of the positive and negative ions of at least about 100,000/cm$^3$ each in the atmosphere in which the positive and negative ions act against the antigenic substance may be selected. In the present specification, the ion concentration means concentration of small ions, and concentration of small ions of which critical mobility is at least 1 cm$^2$/V·sec was measured using an air ion counter (for example, air ion counter (part number 83-1001B) manufactured by Dan Kagaku).

The discharge mechanism here refers to a mechanism having an insulator sandwiched between electrodes, one of which receives a high AC voltage applied thereto and the other is grounded, and by application of the high voltage, plasma discharge occurs in an air layer in contact with the grounded electrode, causing electrolytic dissociation of water molecules or oxygen molecules in the air to generate positive and negative ions. In such a discharge mechanism, when electrode receiving the high voltage is adapted to have a plate shape or meshed shape and the grounded electrode is adapted to have a meshed shape, electric field concentrates at a mesh end surface of the grounded electrode to cause surface discharge, and a plasma region is formed, when a high voltage is applied. When air is introduced to the plasma region, both positive and negative ions are generated.

Devices having such a discharging mechanism include, but not limited to, surface discharge device, corona discharge device, plasma discharge device and the like. Further, the shape and material of the electrodes of discharge device are not limited to those described above, and any shape such as a needle shape, and any material may appropriately be selected.

Figure 7:
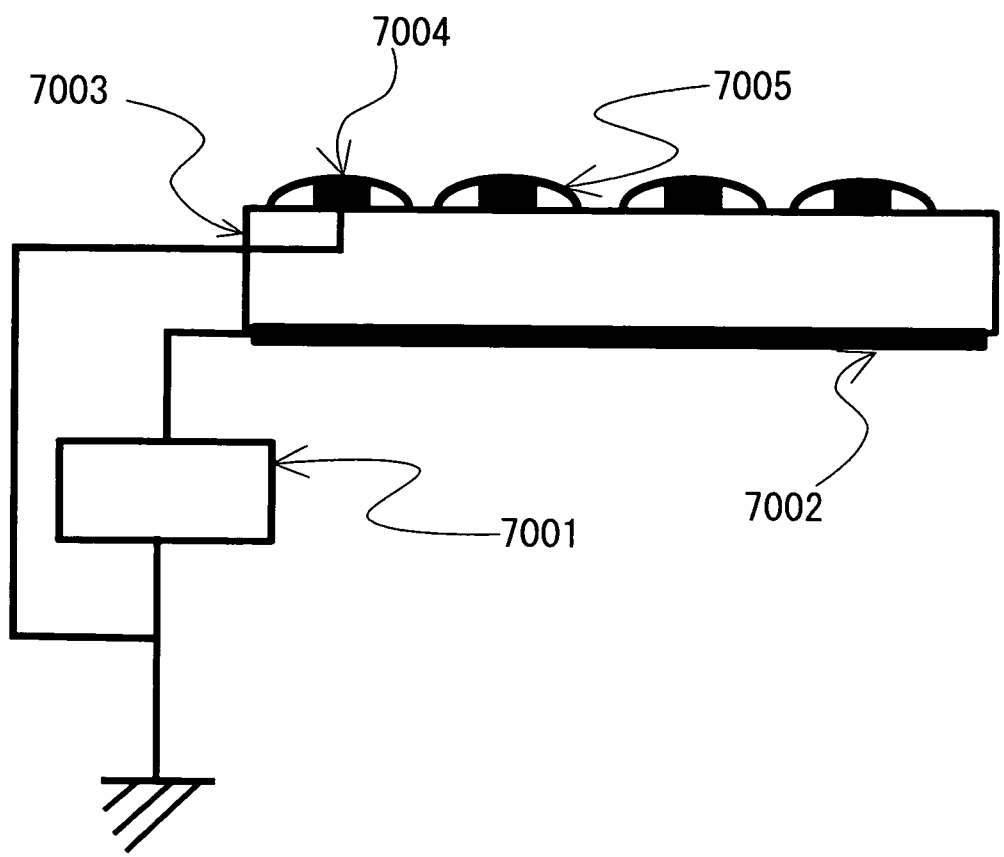
FIG. 7 schematically shows an exemplary structure of an ion generating device used in the present invention.

FIG. 7 schematically shows an exemplary structure of the ion generating device used in the present invention.

Specifically, an ion generating device having such a structure as shown in FIG. 7 is most preferable, in which a dielectric body 7003 is sandwiched between a plate shaped electrode 7002 and a mesh shaped electrode 7004, positive and negative voltages are alternately applied to the plate-shaped electrode from a high voltage power source 7001, whereby electric field concentrates at a mesh end surface of meshed electrode, causing plasma discharge, a plasma region 7005 is formed, and positive and negative ions are generated.

The applied voltage necessary for generating and emitting positive and negative ions may be 2 to 10 kV and preferably 3 to 7 kV as peak-to-peak voltage between electrodes, though it depends on electrode structure.

<Deactivation of Antigenic Substance by Gas Containing Positive and Negative Ions>

The inventors have found that the gas containing both positive and negative ions has a function of deactivating an antigenic substance, as will be described in the examples later, by the method of evaluating performance of the activation gas deactivating the antigenic substance in accordance with the present invention, using the apparatus for generating the processed antigenic substance to be used as the evaluation sample for evaluating the performance of the activation gas deactivating the antigenic substance, in accordance with the present invention.

It is noted, however, that the present invention is not limited to negative and positive ions, and may be used for various gas species of various gas concentrations.

The mechanism for deactivating antigenic substance by the gas containing both positive and negative ions is considered to include not only the mechanism of chemical reaction described above but also a mechanism of deactivation through electric shock caused by the ion generating device that denatures or destroys the antibody-reactive portion of the antigenic substance.

Specifically, the antibody-reactive portion of the antigenic substance is denatured or destroyed also by the plasma discharge itself when the voltage is applied for generating the positive and negative ions, and by such electric shock, the binding capability between the antigenic substance and the antibody is lost, deactivating the antigenic substance.

As described above, by the method of evaluating performance of an activation gas deactivating an antigenic substance, a result suggesting the following fact could be obtained that the antigenic substance can be deactivated by denaturing or destroying the antibody-reactive portion of the antigenic substance through electric shock and/or chemical reaction, and particularly that the antigenic substance can efficiently be deactivated by the synergistic effect of electric shock and chemical reaction.

<Method of Emitting Gas Containing Positive and Negative Ions>

Further, the inventors have found what method of emitting the gas containing positive and negative ions is preferred when the gas containing positive and negative ions is to be used as the activation gas, through the method of evaluating performance of an activation gas deactivating an antigenic substance.

In the present invention, the positive and negative ions are mainly generated by a discharge phenomenon of an ion generating device, and typically, by alternately applying positive and negative voltages, the positive and negative ions can be generated almost simultaneously and emitted to the air. The method of emitting positive and negative ions of the present invention is not limited to this, and it is possible to emit positive or negative ions first by applying either one of positive and negative voltages for a prescribed time period, and to emit ions of the charge opposite to the already emitted ions by applying the other voltage for a prescribed time period.

The applied voltage necessary for generating and emitting positive and negative ions may be 2 to 10 kV and preferably 3 to 7 kV as peak-to-peak voltage between electrodes, though it depends on electrode structure.

It is preferred that the positive ions and negative ions of the present invention are generated under relative humidity of 20 to 90%, and preferably 40 to 70%. As will be described later, generation of positive and negative ions is related to existence of water molecules in the air. Specifically, when the relative humidity is smaller than 20%, clustering of water molecule with an ion at the center does not proceed in a satisfactory manner, and re-combination of ions tend to occur, so that the generated ions come to have shorter life. When it exceeds 90%, dews are formed at the surface of the ion generating device, significantly decreasing efficiency of ion generation. Generated ions are too much clustered and surrounded by many water molecules, and because of thus increased weight, ions cannot reach far but undesirably go down. Therefore, ion generation under too low or too high humidity is not preferable.

The method of emitting positive and negative ions of the present invention is not limited to the discharge phenomenon described above, and a method using a device emitting ultraviolet ray or electronic beam may be used.

<Identification of Positive and Negative Ions>

When the gas containing both positive and negative ions is to be used as the activation gas, the positive and negative ions of the present invention can be generated using oxygen molecules and/or water molecules existing on a surface of a discharge element as raw material. This method of generation does not require any special raw material, and therefore, it is advantageous in view of cost, and in addition, it is preferred as the raw material is harmless and does not generate any harmful ion or substance.

The composition of positive and negative ions generated by the discharge phenomenon by the ion generating device is as follows. The positive ions are mainly derived from water molecules in the air subjected to electrolytic dissociation by plasma discharge, resulting in hydrogen ions $H^+$, which are clustered with water molecules in the air by salvation energy, to form $H_3O^+(H_2O)_n$ (n is 0 or a natural number). Here, $H_3O^+(H_2O)_n$ (n is 0 or a natural number) described as a positive ion can also be described as $H^+(H_2O)_n$ (n is a natural number), and both represent the same ion.

Figure 8A:
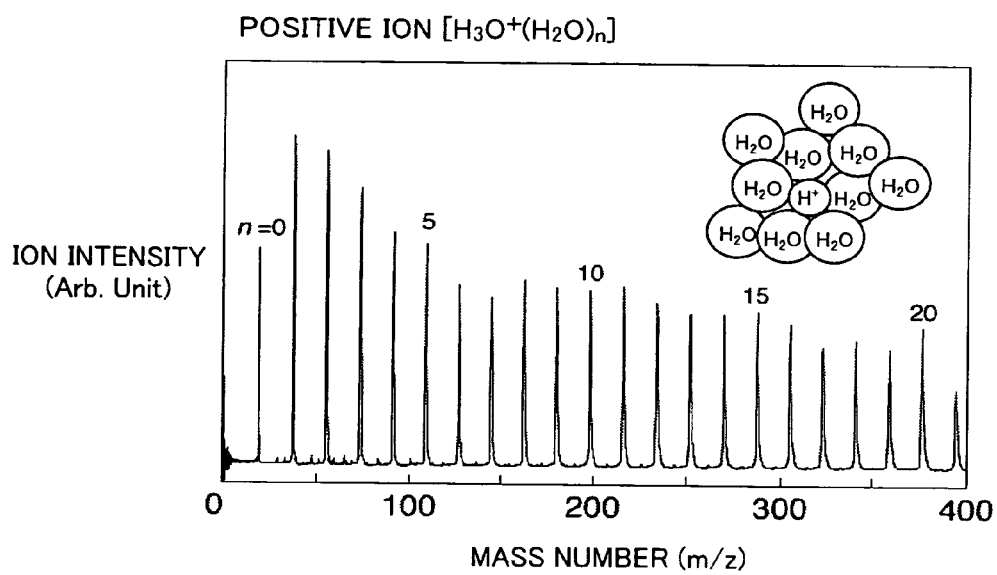
FIGS. 8A and 8B represent mass spectra of positive and negative ions generated from the ion generating device.
Figure 8B:
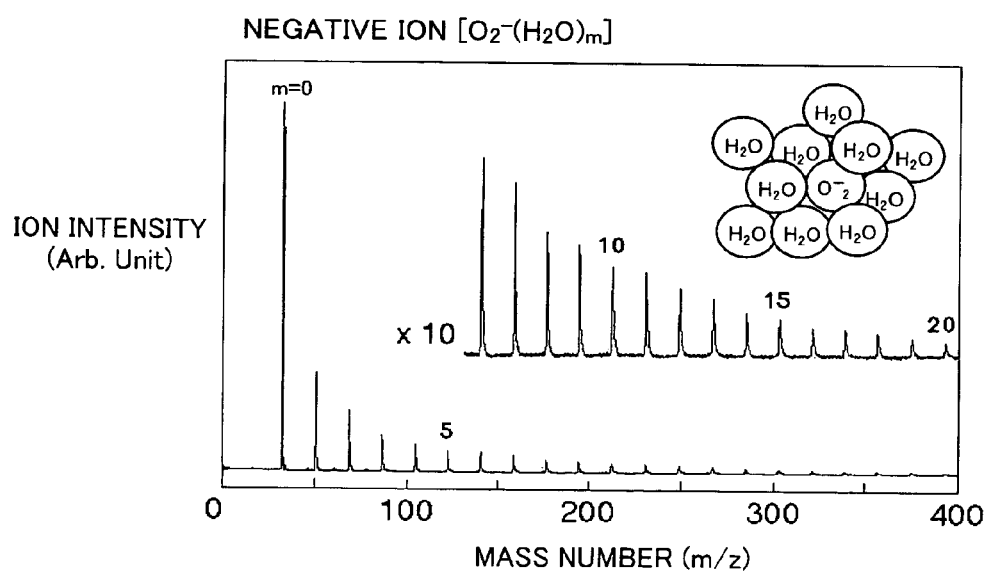

FIGS. 8A and 8B represent mass spectra of positive and negative ions generated from the ion generating device.

That the water molecules are clustered is clearly understood from the fact that the minimum observed peak appears at a position of molecular weight 19 and that the following peaks successively appear at positions apart by water molecular weight of 18 from this molecular weight 19 in FIG. 2A. This result shows that water molecules having molecular weight of 18 are hydrated to a hydrogen ion $H^+$ having the molecular weight of 1 integrally. As for the negative ions, oxygen molecules or water molecules in the air are subjected to electrolytic dissociation by plasma discharge, generating oxygen ions $O_2^-$, which is clustered with water molecules in the air by solvation energy, to form $O_2^-(H_2O)_m$ (m is 0 or a natural number). That the water molecules are clustered is clearly understood from the fact that the minimum observed peak appears at a position of molecular weight 32 and that the following peaks successively appear at positions apart by water molecular weight of 18 from this molecular weight 32 in FIG. 2(b). This result shows that water molecules having molecular weight of 18 are hydrated to an oxygen ion $O_2^-$ having the molecular weight of 32 integrally.

These positive and negative ions emitted to the space surround air-borne antigenic substance, and at the surface of the antigenic substance, the positive and negative ions generate hydrogen peroxide $H_2O_2$, hydrogen dioxide $HO_2$ or hydroxy radical .OH as active spices, through the following chemical reactions (1) and (2).

$$H_3O^+ + O_2^- \rightarrow .OH + H_2O_2 \quad (1)$$

$$H_3O^+ + O_2^- \rightarrow HO_2 + H_2O \quad (2)$$

It is understood that hydrogen peroxide $H_2O_2$, hydrogen dioxide $HO_2$ or hydroxy radical .OH generated by the function of positive and negative ions denature or destroy (decompose) the antibody-reactive portion of antigenic substance, making combination between the antigenic substance and the antibody impossible, whereby the antigenic substance in the air can efficiently be deactivated.

In the foregoing, $H_3O^+(H_2O)_n$ (n is 0 or a natural number) has been mainly described as the positive ion and $O_2^-(H_2O)_m$ (m is 0 or a natural number) has been mainly described as the negative ion. The positive and negative ions of the present invention, however, are not limited to these, and $N_2^+$, $O_2^+$ and the like may be included as positive ions and $NO_2^-$ and $CO_2^-$ may be included as negative ions, with the above-described two positive and negative ions being the main component, and similar effects can be expected.

EXAMPLES

In the following, the present invention will be described in grater detail with reference to the examples. The present invention, however, is not limited to these examples.

<Cedar Pollen>

The cedar pollen was collected from branches of Japanese cedar (scientific name: *Cryptomeria japonica*) grown in Yutakamachi, Hiroshima prefecture. The pollen was collected using a vacuum cleaner with a mesh, and then sifted. After collection, the pollen was stored in a freezer at −30° C.

<Cedar Antigenic Substance>

Eighty grams (80 g) of cedar pollen was stirred in 3.2 L of 20 mM PBS (pH7.4) at 4° C. for 4 hours, and thereafter subjected to centrifugal separation for 30 minutes at 6000 rpm. Thereafter, ammonium sulfate was added to the supernatant to attain final saturated concentration of 80%, and centrifugal separation was performed for 30 minutes at 6000 rpm. After centrifugal separation, dialysis with the duration of 6 hours was repeated 6 times, and centrifugal separation was performed for 30 minutes at 10,000 rpm. After the centrifugal separation, the resulting supernatant was freeze-dried, as the cedar antigenic substance. In the present specification, the cedar antigenic substance is also denoted as CJP.

<Protein Determination by Folin-Lowry Method>

[Composition of Reagents]

Solution A; 1 N of phenol reagent as acid.

Solution B; 2% of $Na_2CO_3$ 0.1 N of NaOH

Solution C; 0.5% of $CuSO_4.5H_2O$

1% of sodium citrate

Solution D; Mixture of B:C=50:1 (v/v)

[Method of Measurement]

A sample of 0.2 ml was mixed with 1 ml of solution D, and left for 10 minutes. Then, 0.1 ml of solution A was added and left for 30 minutes, and light absorption at 750 nm was measured. Further, a standard series was formed with BSA to form a working curve, whereby the amount of protein in the cedar antigenic substance was determined as BSA equivalent.
<Spraying and Recovery of Antigenic Substance>

Cedar antigenic substance (protein concentration 200 ng/ml) extracted from cedar pollen was dispersed using a nebulizer, under ion radiation of positive and negative ions. A recovery vessel was placed at the bottom of the dispersing container, and only the antigen ion-processed without touching the wall surface was recovered. Here, a solution of 8 ml (containing the cedar antigenic substance) was sprayed for 1.5 hours.

Example 1

In the present example, an antigenic substance of cedar pollen was used to confirm lowering of allergic reaction of the antigenic substance by the function of positive and negative ions.

Here, FIG. 2 schematically shows an example of an apparatus for generating a processed antigenic substance used as an evaluation sample for evaluating the performance of an activation gas deactivating an antigenic substance in accordance with the present invention. FIGS. 8A and 8B represent mass spectra of positive and negative ions generated from the ion generating device provided in the apparatus shown in FIG. 2.

First, in the apparatus shown in FIG. 2, a surface discharge device having, a flat shape of 37 mm length and 15 mm width was used as an ion generating device 1021. By alternately applying positive and negative voltages between the electrodes, surface discharge is caused at a surface electrode portion, and by discharge plasma in atmospheric pressure, positive ions 1022 and negative ions 1023 are almost, simultaneously generated and emitted. The applied voltage was 3.3 kV to 3.7 kV in terms of peak-to-peak voltage between the electrodes, and with the voltage in this range, harmful amount of ozone was not generated. Four such ion generating devices were mounted and fixed on a cylindrical semi-sealed container 1027 formed of acryl and having an inner diameter of 150 mm and the length of 370 mm. On one side of the container, an inlet 1028 for spraying a solution containing the antigenic substance is provided, on another side, a recovery vessel 1025 for recovering the solution containing the antigenic substance is provided.

The antigenic substance derived from cedar pollen was used as the antigenic substance, and the cedar pollen was collected from branches of Japanese cedar (scientific name: *Cryptomeria japonica*) grown in Yutakamachi, Hiroshima prefecture. The pollen was collected using a vacuum cleaner with a mesh, and then sifted. After collection, the pollen was stored in a freezer at −30° C. In order to extract the antigenic substance from the cedar pollen, 80 g of cedar pollen was stirred in 3.2 L of 20 mM PBS (pH7.4) at 4° C. for 4 hours, and thereafter subjected to centrifugal separation for 30 minutes at 6000 rpm. Thereafter, ammonium sulfate was added to the supernatant to attain final saturated concentration of 80%, and centrifugal separation was performed for 30 minutes at 6000 rpm. After centrifugal separation, dialysis with the duration of 6 hours was repeated 6 times, and centrifugal separation was performed for 30 minutes at 10,000 rpm. After the centrifugal separation, the resulting supernatant was freeze-dried, and provided as the cedar antigenic substance solution.

The thus obtained antigenic substance solution of 8 ml was put in a nebulizer 1024, which was connected to inlet 1028 for spraying antigenic substance solution of the apparatus shown in FIG. 2. The recovery vessel 1025 for recovering the antigenic substance solution of the apparatus was placed on the bottom of cylindrical semi-sealed container 1027. The nebulizer was connected to an air compressor and sprayed the thus obtained antigenic substance through inlet 1028, using compressed air (flow rate 5 L/min). The amount sprayed was 8.0 ml (duration: 90 min). After 90 minutes, the antigenic substance sedimented at the bottom of cylindrical semi-sealed container was recovered by the recovery vessel. It took about 90 seconds for the sprayed antigenic substance to naturally fall, while reacting with the positive ions 1022 and negative ions 1023 in the air.

Reactivity with the serum IgE antibody taken from hey fever patients was measured by ELISA method. The concentrations of positive and negative ions in the atmosphere were measured by introducing air at the flow rate of 5 L/min by an air compressor through inlet 1028 of cylindrical semi-sealed container 1027 for spraying antigenic substance solution with ion generating devices 1021 mounted, and by placing air ion counter (part number 83-1001B) manufactured by Dan Kagaku at recovery vessel 1025 for recovering the antigenic substance solution, measuring the total positive and negative ion concentrations in the space. The atmosphere in the space had the temperature of 25° C. and relative humidity of 60% RH. As shown in FIGS. 8A and 8B, respectively, it was considered that the emitted positive ions were $H_3O^+$ $(H_2O)_n$ (n is 0 or an arbitrary natural number) and negative ions were $O_2^-$ $(H_2O)_m$ (m is 0 or a natural number), and that these positive and negative ions generate hydrogen peroxide $H_2O_2$, hydrogen dioxide $HO_2$ or hydroxy radical .OH by the chemical reactions (1) and (2) described above.

Reduction in allergic reaction between the antigenic substance and the IgE antibody was studied, for the unprocessed state with the ion generating device 1021 not operated, and when voltage of 3.3 kV to 3.7 kV as the peak-to-peak voltage between electrodes was applied to emit positive and negative ions and the concentrations of positive and negative ions were each 100,000/cm$^3$, in the cylindrical semi-sealed container 1027. Results are as shown in FIGS. 9A, 9B and 10A, 10B.

Figure 9A:
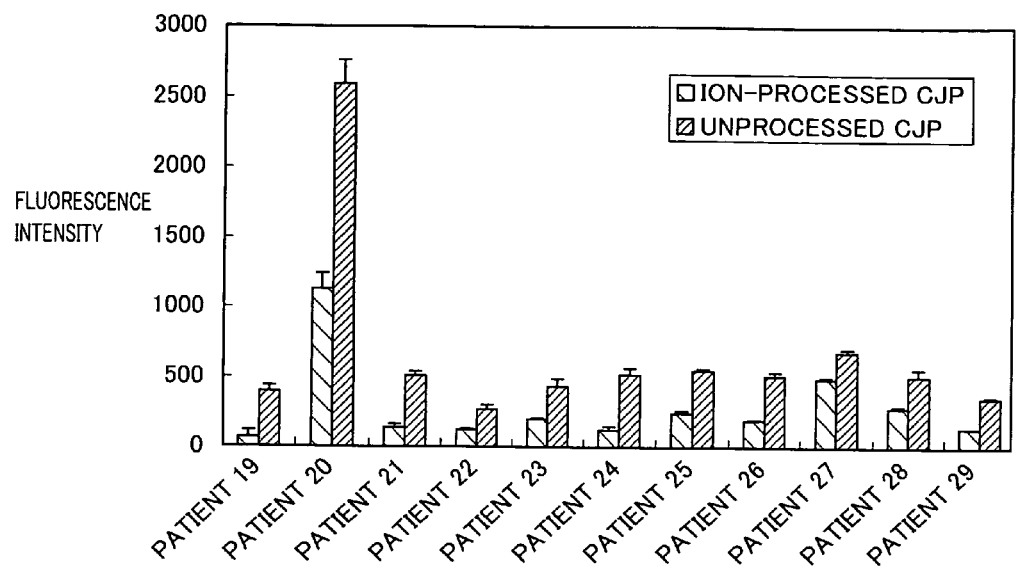
FIGS. 9A and 9B represent relation of allergic reaction of serum IgE antibody and cedar antigenic substance processed and unprocessed with a gas containing positive and negative ions of hay fever patients 19 to 40.
Figure 9B:
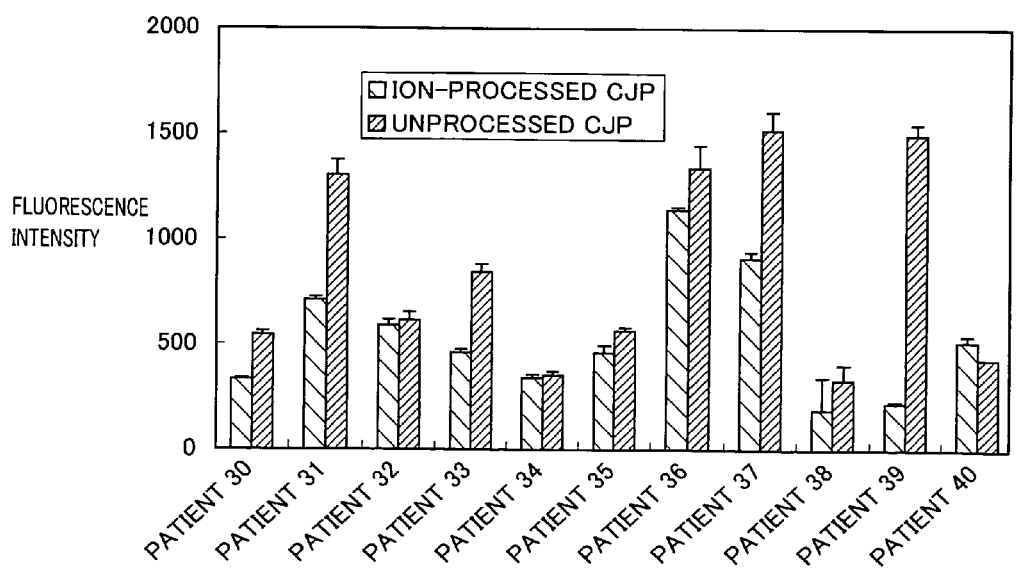

FIGS. 9A and 9B represent relation of allergic reaction of serum IgE antibody and cedar antigenic substance processed and unprocessed with a gas containing positive and negative ions of hay fever patients 19 to 40.

Figure 10A:
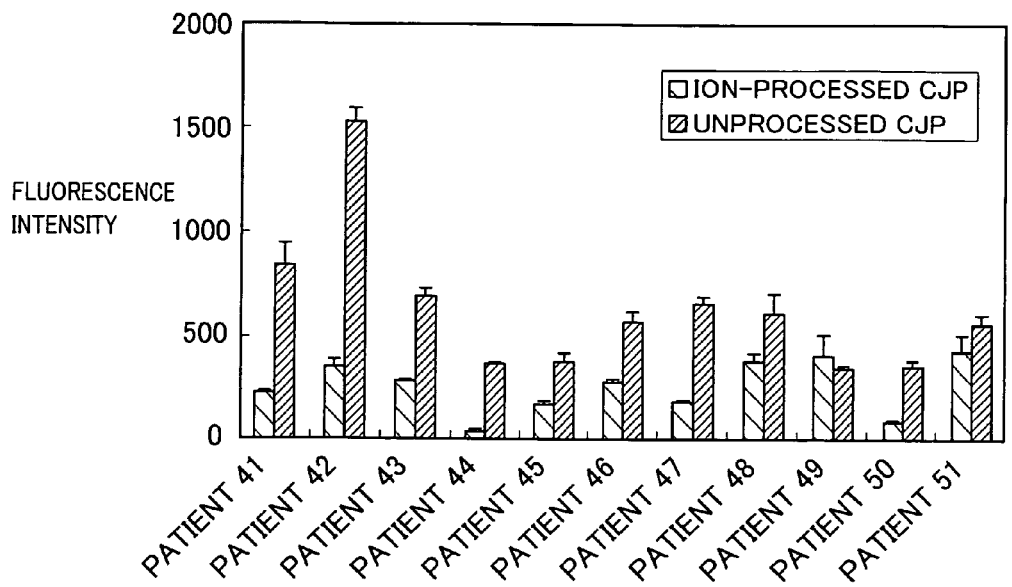
FIGS. 10A and 10B represent relation of allergic reaction of serum IgE antibody and cedar antigenic substance processed and unprocessed with a gas containing positive and negative ions of hay fever patients 41 to 60.
Figure 10B:
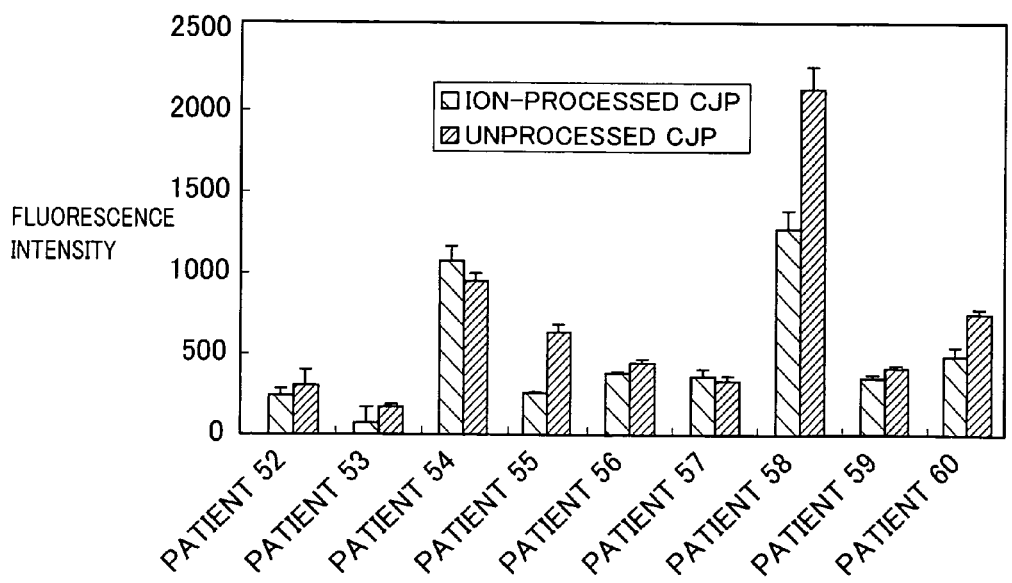

FIGS. 10A and 10B represent relation of allergic reaction of serum IgE antibody and cedar antigenic substance processed and unprocessed with a gas containing positive and negative ions of hay fever patients 41 to 60.

As shown in FIGS. 9A, 9B, 10A and 10B, when we compare the case where the ion generating device was not operated (that is, a state in which positive and negative ions are not generated) and the case when the concentrations of positive and negative ions were each 100,000/cm$^3$, it was confirmed that among 42 hey fever patients, 33 exhibited significant decrease in reactivity (binding characteristic) of serum IgE of hey fever patients.

Decrease in reactivity of Cry j 1 and Cry j 2 monoclonal antibody with serum IgE antibody was studied, where ion generating device was not operated and where a voltage of 3.3 kV to 3.7 kV was applied as peak-to-peak voltage between electrodes of the device to emit positive and negative ions to attain concentration of 100,000/cm$^3$ for each of positive and negative ions in cylindrical semi-sealed container 1027 after spraying by nebulizer. The results are as shown in FIG. 11.

Figure 11:
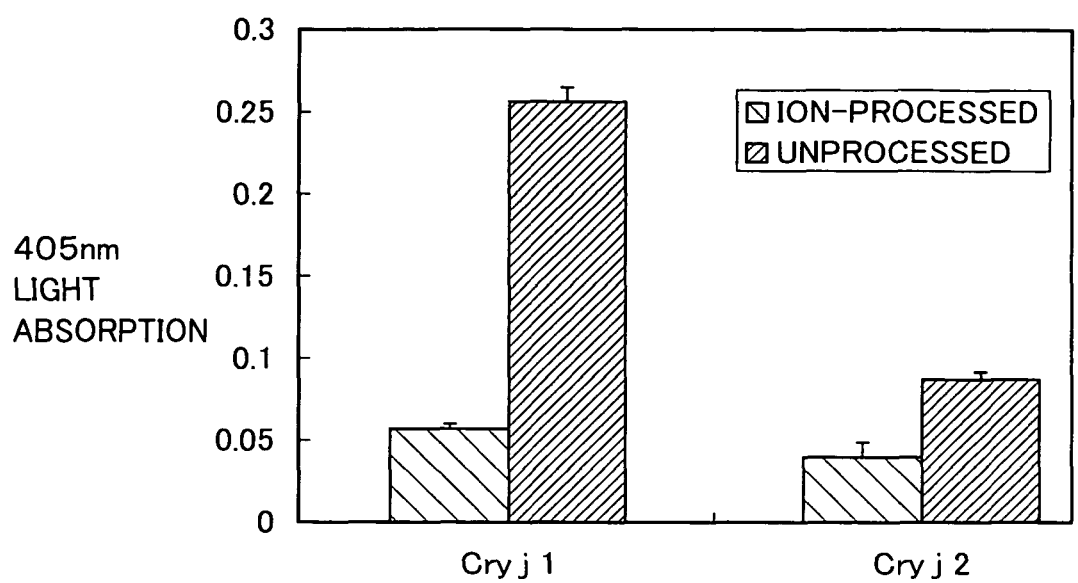
FIG. 11 represents relation of reactivity between Cry j 1 and Cry j 2 and monoclonal antibody thereof, with cedar antigenic substance processed and unprocessed with a gas containing positive and negative ions.

FIG. 11 represents relation of reactivity between Cry j 1 and Cry j 2 and monoclonal antibody, with cedar antigenic substance processed and unprocessed with a gas containing positive and negative ions.

When we compare the case where the ion generating device was not operated (that is, a state in which positive and negative ions are not generated) and the case when the concentrations of positive and negative ions were each 100,000/cm$^3$, it was confirmed that reactivity (binding characteristic) of serum IgE of hey fever patients, that is, reactivity of Cry j 1 and Cry j 2 monoclonal antibody with serum IgE antibody was significantly decreased when ion processing was performed.

For quantitative evaluation of difference in reactivity between ion-processed and unprocessed cedar antigenic substances and serum IgE of hey fever patients, ELIZA inhibition (enzyme-liked immunosorbent assay inhibition) method was used.

Specifically, the cedar antigenic substance recovered after spraying was put in a centrifugal separator (Centriprep YM-10), and subjected to centrifugal condensation at 2500 rpm. Further, the condensation was put in a centrifugal separator (ULTRA FLEE-MC) and subjected to centrifugal condensation at 7000 rpm. Condensed ion-processed cedar antigenic substance and condensed unprocessed cedar antigenic substance were 5-times diluted from protein concentration of 11 μg/ml for 8 times. The diluted antigenic substances, 50 μl each, were mixed with 50 μl of 10-times diluted serum IgE of each patient, and pre-incubated overnight at 4° C.

Specifically, using a 96-well plate for ELISA, 50 μl of cedar antigenic substance (not even sprayed) diluted to 1 μg/ml with bicarbonate buffer solution was applied to a well, and left still for 2 hours. The plate was washed three times with washing buffer solution, and then, 300 μl of blocking buffer solution was applied and left still overnight at 4° C. Then, the plate was washed three times, and pre-incubated samples were applied, 50 μl per well, and left still for 4 hours.

The plate was washed three times, and biotin-labeled anti-human IgE diluted 1000 times with (3% of skim milk+1% of BSA)/PBST was applied, 50 μl per well, and left still for 2.5 hours. The plate was washed three times, 50 μl of alkali phosphatase labeled streptavidin diluted 1000 times with (3% of skim milk+1% of BSA)/PBST was applied, and left still for 1.5 hours at a room temperature.

The plate was washed four times, Attophos™ substrate buffer was applied, 50 μl per well, and left until colored, with light shielded. Fluorescent intensity was measured using Cyto™ FluorII. Reactivity (binding characteristic) of serum IgE antibody of hey fever patients was studied, where ion generating device was not operated and ion processing was not done and where a voltage of 3.3 kV to 3.7 kV was applied as peak-to-peak voltage between electrodes of the device to emit positive and negative ions to attain concentration of 100,000/$cm^3$ for each of positive and negative ions in cylindrical semi-sealed container 1027. The results are as shown in FIG. 12.

FIG. 12 represents relation of allergic reaction between the antigenic substance and the serum IgE antibody of hey fever patients, with cedar antigenic substance processed and unprocessed with a gas containing positive and negative ions, by ELISA inhibition method.

When the ion generating device was not operated (that is, in a state where positive and negative ions were not generated), the amount of cedar antigenic substance necessary for 50% inhibition was about $2.53\times10^3$ pg, and when each of positive and negative ion concentrations was 100,000/$cm^3$, the amount of cedar antigenic substance necessary for 50% inhibition was $1.34\times10^4$ pg, and therefore, the ratio of deactivation was confirmed to be 81%.

Each of ion-processed and unprocessed cedar antigenic substances was diluted to protein concentration of 0.5 μg/ml with 0.9% of NaCl, and 0.02 ml of the resulting sample was injected to cedar hey fever patients on their inner forearm, using a syringe for tubercline test. After about 15 minutes, longer and shorter diameters of appeared erythema and wheal were measured, and reactivity was evaluated from the average diameter. The results are as shown in Table 1

TABLE 1

| | Intradermal Reaction Test | | Conjunctival Reaction Test | |
|---|---|---|---|---|
| Patient | Unprocessed | Ion-processed | Unprocessed | Ion-processed |
| A | +++ | + | − | − |
| B | +++ | + | + | − |
| C | +++ | + | + | − |
| D | +++ | + | + | − |
| E | +++ | + | + | − |
| F | +++ | + | + | − |

Here, "−" denotes that reddish area or erythema<10 mm, "±" denotes reddish area of 10 mm to 20 mm, "+" denotes reddish area of 20 mm to 30 mm or swelling or wheal<10 mm, "++" denotes reddish area of 30 mm to 40 mm or swelling of 10 mm to 14 mm, and "+++" denotes reddish area>40 mm or swelling>15 mm or swelling with pseudopod. As can be seen from Table 1, when the unprocessed case where the ion generating device was not operated (that is, positive and negative ions are not generated) and the case where processing was done in an atmosphere having positive and negative ion concentrations of 100,000/$cm^3$ each were compared, it could be confirmed that the hey fever patients had the intradermal reaction soothed significantly.

Further, ion-processed cedar antigenic substance and unprocessed cedar antigenic substance were diluted to protein concentration of 5 μg/ml with 0.9% of NaCl, and 5 μl of the resulting sample was dripped to the eyes of cedar hey fever patients using a pipet. After about 15 minutes, conjunctival reactions appeared as congestion of plica semilunaris, lid and bulbar conjuctiva, itch, lacrimation and the like were observed. The determination is as follows: "−" denotes no congestion, "±" denotes slight congestion and itching, "+" denotes congestion either at an upper or lower portion of the conjunctiva, "++" denotes congestion both at upper and lower portions of the conjunctiva, "+++" denotes congestion entirely over the conjunctiva, and "++++" denotes eyelid edema and the like. The results are also shown in Table 1.

As shown in Table 1, when the unprocessed case where the ion generating device was not operated (that is, positive and negative ions are not generated) and the case where processing was done in an atmosphere having positive and negative ion concentrations of 100,000/$cm^3$ each were compared, it could be confirmed that hey fever patients had the conjectival reaction soothed significantly.

Example 2

Using the serum IgE of patient #19 subjected to the ELIZA method above as an antibody, fluorescence intensity of unprocessed cedar antigenic substance and ion-processed cedar antigenic substance were found by the ELIZA method in the similar manner as described above (specifically, the apparatus of FIG. 3 was used, and for ion-processing, concentration of 100,000/$cm^3$ was attained both for positive and negative ions), with four different concentrations (in terms of protein concentrations) of the antigenic substance (cedar antigenic substance) of 100 ng/ml, 200 ng/ml, 400 ng/ml and 800 ng/ml. From the fluorescence intensity, ratio of deactivation of allergic reaction was calculated in accordance with equation (3) below. The results are as shown in Table 2 below.

TABLE 2

| | Concentration of antigenic substance (ng/ml) | | | |
|---|---|---|---|---|
| | 100 | 200 | 400 | 800 |
| Ratio of deactivation (%) | 94 | 83 | 78 | 56 |

Ratio of deactivation %=$(1-C/D)\times 100$         (3)

C: Fluorescence intensity of ion-processed cedar antigenic substance

D: Fluorescence intensity of unprocessed cedar antigenic substance

Thereafter, selecting the sample having the antigenic substance concentration of 200 ng/ml as a reference, assuming that the following relation holds between the ion concentration and the concentration of the antigenic substance, relation between the positive and negative ion concentrations and the ratio of deactivation was calculated.

Specifically, if the ratio of deactivation were constant, there would be a prescribed relation held between the ion concentration and the concentration of the antigenic substance concentration. For example, when the ion concentration is kept constant and the concentration of the antigenic substance is decreased to one half and when the concentration of the antigenic substance is kept constant and the ion concentration was doubled, it follows that the same ratio of deactivation results. Therefore, using the two points that the ion concentrations of positive and negative ions are each 100,000/cm$^3$ and that the concentration of the antigenic substance is 200 ng/ml as references, the relation between the positive and negative ion concentrations and the ratio of deactivation is plotted in FIG. 13. Specifically, the data obtained when the positive/negative ion concentrations were 25,000/cm$^3$, 50,000/cm$^3$, 100,000/cm$^3$ and 200,000/cm$^3$ correspond to the data obtained when the concentrations of the antigenic substance in accordance with ELIZA method described above were 800 ng/ml, 400 ng/ml, 200 ng/ml and 100 ng/ml, respectively (in FIG. 13, the abscissa represents each of positive and negative ion concentrations).

Figure 13:
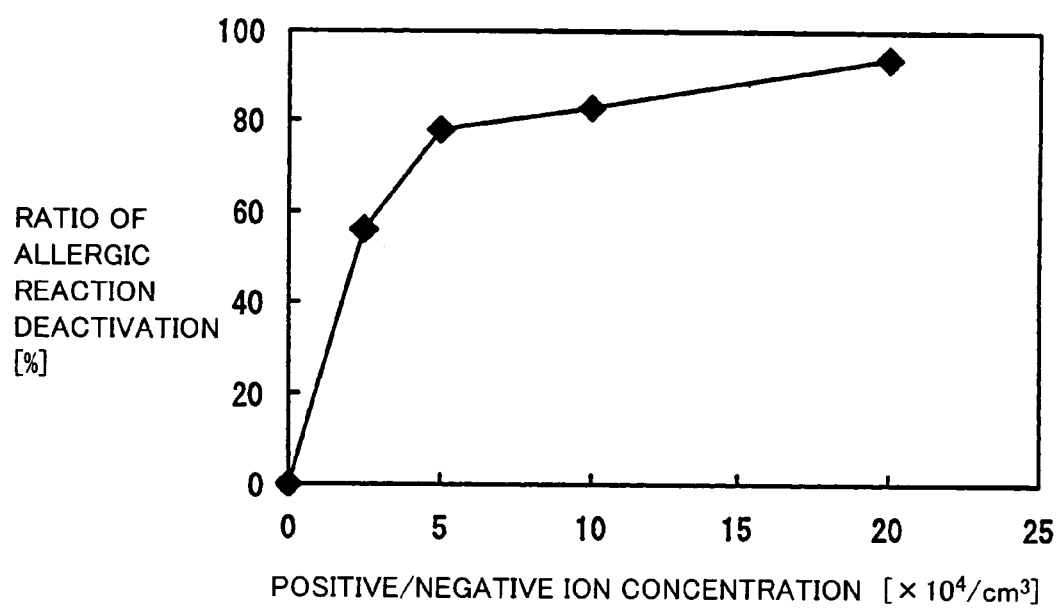
FIG. 13 represents relation between concentrations of positive/negative ions of the activation gas and ratio of deactivation of an antigenic substance derived from cedar pollen.

As is apparent from FIG. 13, when the positive/negative ion concentration increases, the ratio of deactivation also increases, and when each of the positive and negative ion concentrations is 50,000/cm$^3$, reaction deactivation as high as about 78% can be attained, realizing stable effect of deactivating the antigenic substance. When each of the positive and negative ion concentrations is 100,000/cm$^3$, reaction deactivation as high as about 83% can be attained, and when each of the positive and negative ion concentrations is 200,000/cm$^3$, reaction deactivation as high as about 94% can be attained, so that it becomes possible to effectively suppress allergic disease such as hey fever or mite allergy.

In Examples 1 and 2, a gas containing both positive and negative ions is used as the activation gas, and an antigenic substance derived from cedar pollen is used as the antigenic substance. By using the method of evaluating performance of an activation gas deactivating an antigenic substance of the present invention, however, the performance of activation gases of other types deactivating other types of antigenic substances can be evaluated accurately in a simple manner.

Further, in Examples 1 and 2, the processed antigenic substance was generated using the apparatus for generating the processed antigenic substance to be used as an evaluation sample for evaluating performance of an activation gas deactivating an antigenic substance of the present invention shown in FIG. 2. The processed antigenic substance may be generated using the apparatuses shown in FIGS. 3 to 6, and the performance of an activation gas deactivating an antigenic substance can be evaluated accurately in a simple manner as above.

Example 3

In this example, deactivation of antigenic substance by the function of positive and negative ions was confirmed, using mite dust antigenic substance. Description will be given in the following with reference to FIGS. 14 and 15.

FIG. 14 is a schematic diagram of an apparatus for executing a method of deactivating antigenic substance by the function of positive and negative ions. FIG. 15 represents evaluation of reactivity between mite antigenic substance (referred to as Derf) and serum IgE of 18 patients a to r, by ELIZA method. The apparatus of FIG. 14 includes the ion generating device shown in FIG. 7 as in the apparatus of FIG. 2, and mass spectra of positive and negative ions emitted therefrom are as shown in FIGS. 8A and 8B, respectively.

<Apparatus for Executing Method of Deactivating Antigenic Substance>

First, the apparatus shown in FIG. 14 used in the present example is similar to that shown in FIG. 2 (and therefore, the same or corresponding portions are denoted by the same reference characters in FIGS. 2 and 14), except that equipment for reducing ozone concentration is additionally provided. Specifically, in the apparatus shown in FIG. 14, one exhaustion outlet 1026 and nebulizer 1024 are connected with a filter 1029 interposed. Filter 1029 includes activated carbon and a molecular sieve, and has a function of removing ozone generated in the cylindrical sealed container 1027. Therefore, the ozone concentration in cylindrical sealed container 1027 is kept at 0.025 ppm or lower.

In the apparatus shown in FIG. 14, similar to the apparatus shown in FIG. 2, the antigenic substance 1038 is sprayed from inlet 1028 and falls naturally to recovery vessel 1025, while the substance is exposed to positive and negative ions and reacts therewith.

<Mite Dust and Antigenic Substance>

As the antigenic substance, antigenic substance extracted from mite dust was used. The mite dust was collected from ordinary household, captured from cushions and carpets by a vacuum cleaner with a mesh.

In order to extract the antigenic substance from the mite dusts, 0.1 g of mite dust was stirred in 15 mL of 20 mM phosphate buffer solution (PBS, pH 7.4) for 16 hours at 4° C., and filtered through a membrane filter (0.2 μm), and the result was used as the mite antigenic substance. The mite antigenic substance includes Derf 1 and Derf 2, as antigenic substances.

<Protein Determination by Folin-Lowry Method>

A solution containing the mite antigenic substance, 0.2 ml, was mixed with 1 ml of solution D, as will be described later, and left for 10 minutes. Thereafter, solution A, as will be described later, was added by 0.1 ml and left for 30 minutes, and thereafter, light absorption was measured at 750 nm. Further, a standard series was formed with bovine serum albumin (BSA) to form a working curve, whereby the amount of protein in the mite antigenic substance was determined as BSA equivalent. As a result, protein concentration was 94.1 ng/ml. Reagents used here are as follows.

(Reagents)

Solution A; 1N of phenol reagent as acid.

Solution B; 2% of $Na_2CO_3$+0.1 N of NaOH

Solution C; 0.5% of $CuSO_4.5H_2O$+1% of sodium citrate
Solution D; Solution B: Solution C=50:1 (v/v)
<Spraying and Recovery of Antigenic Substance>

Figure 14:
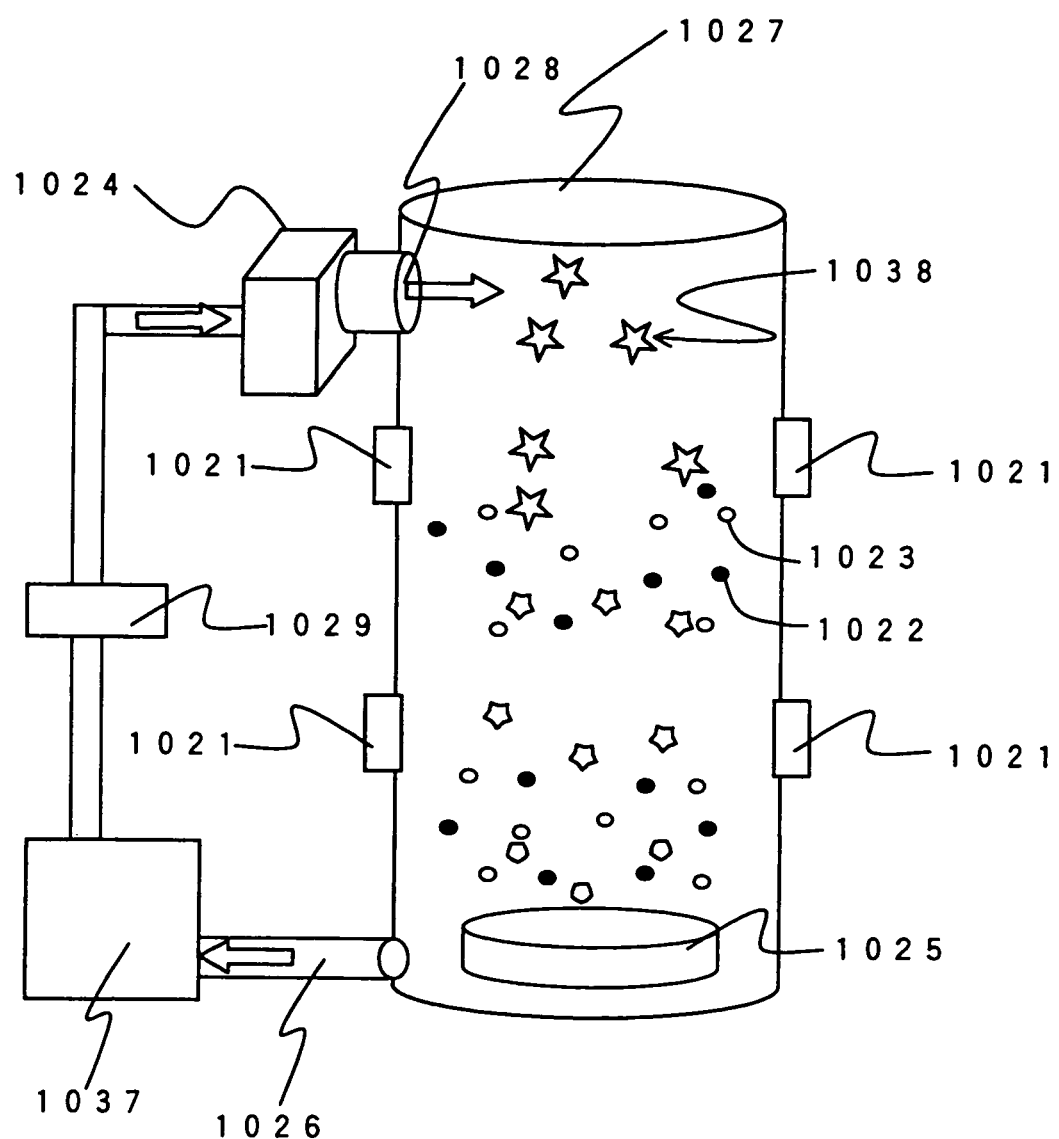
FIG. 14 is a schematic diagram showing an apparatus for executing the method of deactivating antigenic substance, having a mechanism for decreasing ozone concentration.

The solution containing mite antigenic substance as the antigenic substance obtained in this manner (protein concentration 200 ng/ml) of 8 ml was put in a nebulizer 1024, which was connected to inlet 1028 of the apparatus shown in FIG. 14 for spraying antigenic substance solution. In order to recover the sprayed solution containing antigenic substance, recovery vessel 1025 was placed at the bottom of cylindrical sealed container 1027.

The nebulizer was connected to an air compressor and sprayed the antigenic substance 1038 through inlet 1028, using compressed air (flow rate 5 L/min). The amount sprayed was 8.0 ml (duration: 90 min). After 90 minutes, the antigenic substance sedimented at the bottom of cylindrical sealed container 1027 was recovered by recovery vessel 1025. It took about 90 seconds for the sprayed antigenic substance 1038 to naturally fall through cylindrical sealed container 1027.

Such spraying and recovery of antigenic substance was performed twice, with the ion generating device 1021 in operation (that is, with ion-processing) and not in operation (that is, without ion-processing).

When ion generating device 1021 was operated so that positive and negative ions reacted against the antigenic substance, the concentrations of positive and negative ions in the atmosphere (in cylindrical sealed container 1027) were measured by introducing air at the flow rate of 5 L/min by an air compressor through inlet 1028 of cylindrical sealed container 1027 for spraying antigenic substance solution, with ion generating devices 1021 mounted, and by placing air ion counter (part number ITC-201A) manufactured by Andes Denki at recovery vessel 1025 for recovering the antigenic substance solution, measuring the positive and negative ion concentrations. As a result, when voltage of 3.3 kV to 3.7 kV as the peak-to-peak voltage between electrodes was applied to ion generating devices 1021, the concentration of positive and negative ions was each 100,000/$cm^3$, in the cylindrical sealed container 1027. The atmosphere in the space had the temperature of 25° C. and relative humidity of 60% RH. As shown in FIGS. 8A and 8B, respectively, it was considered that the emitted positive ions were $H_3O^+$ $(H_2O)_n$ (n is 0 or a natural number) and negative ions were $O_2^-$ $(H_2)_m$ (m is 0 or a natural number), and that these positive and negative ions generate hydrogen peroxide $H_2O_2$, hydrogen dioxide $HO_2$ or hydroxy radical .OH by the chemical reactions (1) and (2) described above.

<Reactivity Evaluation by ELISA Method>

Next, reactivity between the mite antigenic substance collected in this manner and the serum IgE antibody taken from mite allergy patients a to r was measured by ELISA (enzyme-liked immunosorbent assay) method. As for the antigenic substance, those reacted with positive and negative ions (ion-processed mite antigenic substance) and not reacted (unprocessed mite antigenic substance) were compared to evaluate the reactivity.

Specifically, using a 96-well plate for ELISA, ion-processed mite antigenic substance and unprocessed mite antigenic substance diluted to 0.1 μg/ml with bicarbonate buffer solution were applied, 50 μl per well. At the same time, human IgE standard double-diluted five times from 200 μg/ml with bicarbonate buffer solution was applied, 50 μl per well, and left still for 2 hours at a room temperature. The plate was washed three times with washing buffer, and a blocking buffer of 300 μl was applied and left still overnight at 4° C.

After left still for one night, the plate was washed three times, serum of mite allergy patient diluted 20 times with (3% of skim milk+1% of BSA)/PBST and incubated for one hour was applied, 50 μl per well, and left still for 4 hours. The plate was washed three times, and biotin-labeled anti-human IgE diluted 1000 times with (3% of skim milk+1% of BSA)/PBST was applied, 50 μl per well, and left still for 2 hours.

After left still, the plate was washed four times, 50 μl of alkali phosphatase labeled streptavidin diluted 1000 times with (3% of skim milk+1% of BSA)/PBST was applied, and left still for one hour at a room temperature. The plate was washed five times, Attophos (trademark) substrate buffer was applied, 50 μl per well, and left until colored, with light shielded. Fluorescent intensity was measured using a spectrophotometer (Cyto (trademark) FluorII). Results are as shown in FIG. 15.

Figure 15:
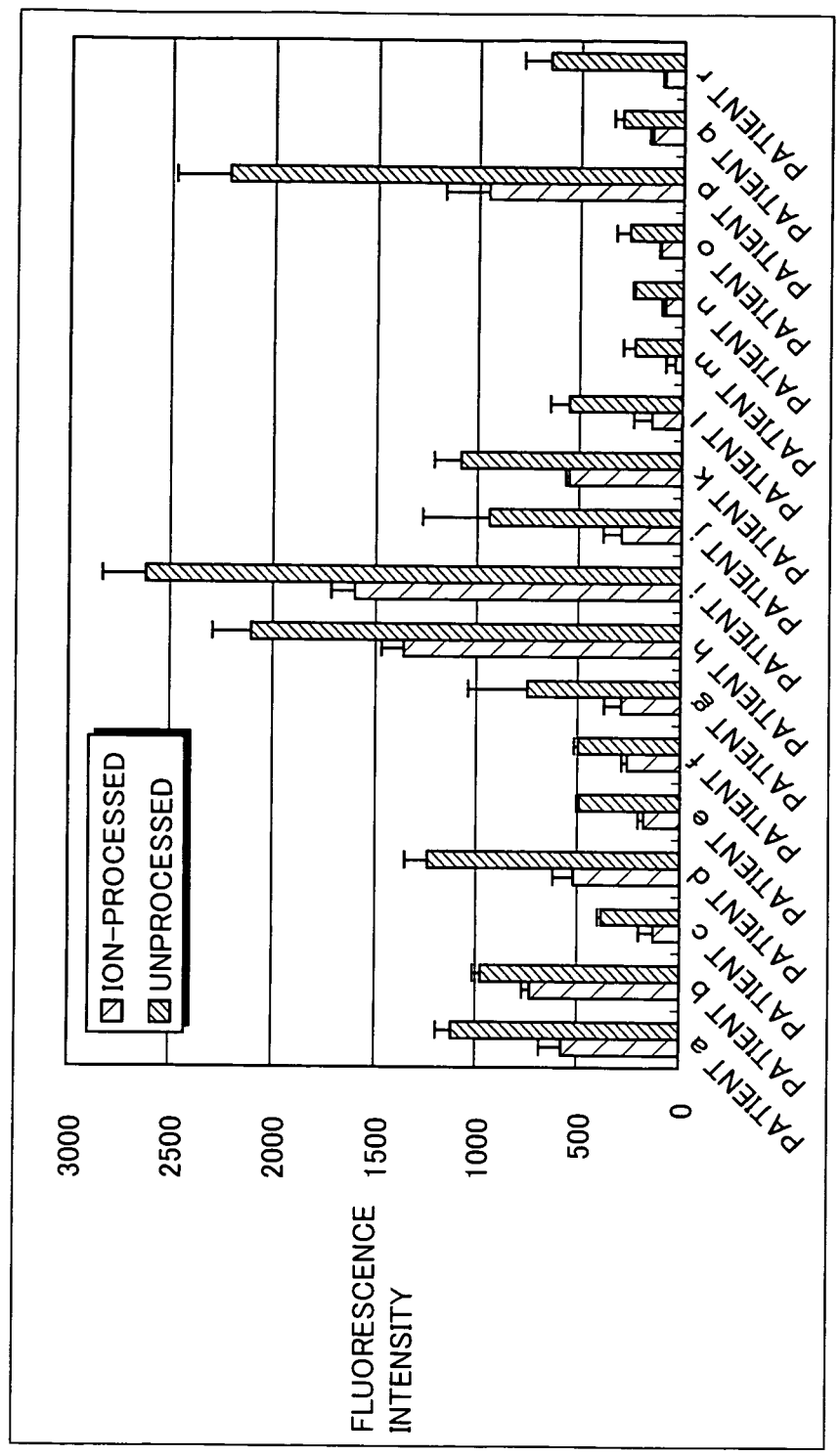
FIG. 15 represents relation of allergic reaction of serum IgE antibody and ion-processed and unprocessed antigenic substances (mite antigenic substance) of mite allergy patients a to r.

As shown in FIG. 15, reactivity (binding characteristic) between serum IgE antibody of mite allergy patients and mite antigenic substance where the ion generating device 1021 was not operated (that is, positive and negative ions were not generated and ion-processing does not occur) and where concentrations of positive and negative ions were both 100,000/$cm^3$ was confirmed. All 18 mite allergy patients a to r exhibited significant decrease in reactivity between the ion-processed antigen and the serum IgE antibody of the patients (lower fluorescence intensity represents lower reactivity). Reagents used here are as follows.

(Reagents)
Sodium hydrogen carbonate buffer solution; 100 mM of $NaHCO_3$ (pH 9.2~9.5)
Phosphate buffer solution (PBS); 4 g of NaCl, 0.1 g of $Na_2HPO_4.12H_2O$, 1.45 g of KCl, 1 g of $KH_2PO_4$, mixed with distilled water to 500 ml
PBST; PBS+0.5% of Tween-20
Blocking buffer solution; PBS+3% of skim milk+1% of BSA
Washing buffer solution; 43 g of $Na_2HPO_4.12H_2O$, 3.6 g of $NaH_2PO_4$, 263 g of NaCl, 15 ml of Tween-20, mixed with distilled water to 3 L.

<Ratio of Deactivation>

Using serum IgE of patients a to r described with reference to the ELIZA method above as the antibody, fluorescence intensities of unprocessed mite antigenic substance and ion-processed mite antigenic substance were found by the ELIZA method, and from the fluorescence intensities, the ratio of deactivation of allergic reaction was calculated in accordance with the following equation (4). The results are as shown in Table. 3.

TABLE 3

| Patient | Fluorescence Intensity | |
| --- | --- | --- |
| | Unprocessed Average | Ion-processed Average |
| a | 1903.333 | 1355.330 |
| b | 977.333 | 734.667 |
| c | 890.333 | 633.333 |
| d | 1541.667 | 819.333 |
| e | 790.333 | 472.667 |
| f | 982.667 | 742.000 |
| g | 1565.667 | 1101.330 |
| h | 3100.333 | 2354.670 |
| i | 3524.667 | 2505.000 |
| j | 1565.000 | 915.000 |
| k | 1808.000 | 1274.670 |
| l | 1232.333 | 830.000 |
| m | 562.000 | 368.333 |
| n | 439.667 | 292.333 |
| o | 661.333 | 508.000 |

TABLE 3-continued

| | Fluorescence Intensity | |
|---|---|---|
| Patient | Unprocessed Average | Ion-processed Average |
| p | 2658.667 | 1395.670 |
| q | 607.667 | 460.000 |
| r | 1448.000 | 884.667 |

Ratio of deactivation %=$(1-E/F)\times 100$ (4)

E: Fluorescence intensity of ion-processed mite antigenic substance

F: Fluorescence intensity of unprocessed mite antigenic substance

As is apparent from Table 3, average ratio of deactivation among patients a to r was 57.8%, and therefore, it is expected that mite allergic disease could effectively be suppressed.

Example 4

Figure 12:
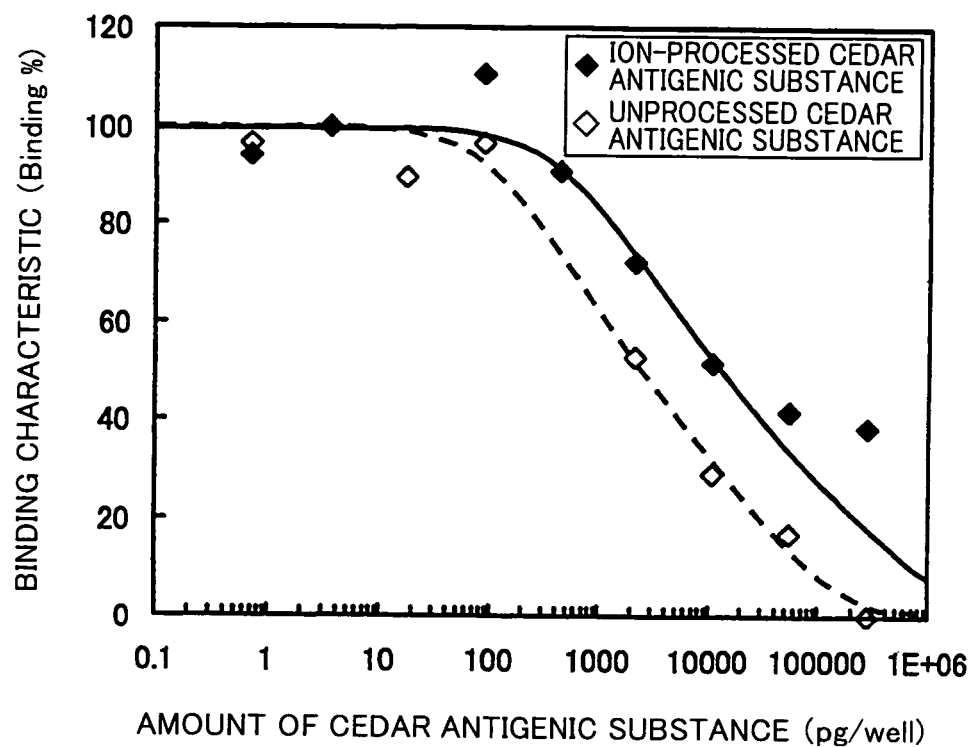
FIG. 12 represents relation of allergic reaction between the antigenic substance and the serum IgE antibody of hey fever patients, with cedar antigenic substance processed and unprocessed with a gas containing positive and negative ions, by ELISA inhibition method.

In this example, deactivation of mite dust (antigenic substance contained therein) by the function of positive and negative ions was confirmed, directly using mite dust. Description will be given in the following with reference to FIGS. 11 to 13. Determination of protein mass in the mite antigenic substance included in mite dust by Folin-Lowry method was performed in the similar manner as in Example 3.

<Diffusion and Recovery of Mite Dust>

Figure 16:
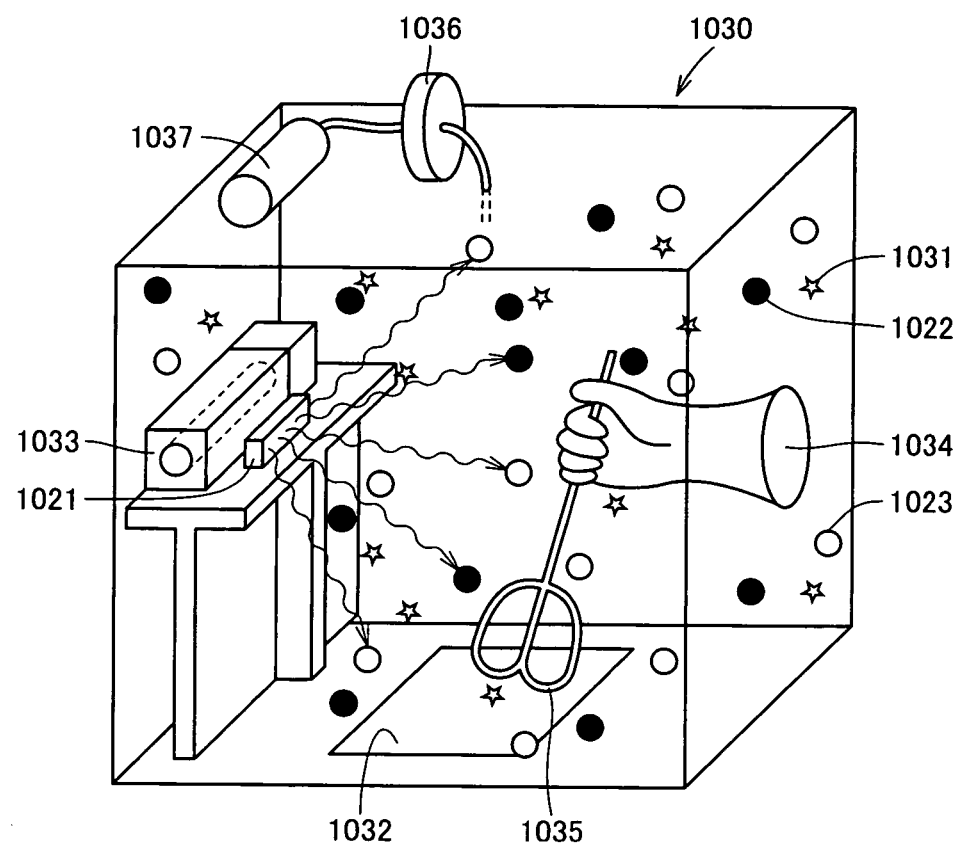
FIG. 16 is a schematic diagram showing an exemplary apparatus for executing the method of deactivating an antigenic substance, including a blower and a recovery filter.

Mite dust was diffused and recovered using an apparatus shown in FIG. 16 (in FIG. 16, portions denoted by the same reference characters as in other figures denote the same or corresponding portions). Specifically, the apparatus is formed of a sealed box 1030 having a blower 1033 and an operating window 10334, and at an air outlet of blower 1033, ion generating device 1021 is mounted.

First, both ion generating device 1021 and blower 1033 were operated. The operation condition was as follows: the peak-to-peak voltage between electrodes of ion generating device 1021 was adjusted to 90V so that the spatial average concentrations of positive and negative ions each attain 3000/cm$^3$, and fan flow rate of blower 1033 was set to 2 m$^3$/min.

The spatial average concentrations of both positive and negative ions in box 1030 were measured by measuring concentrations of positive and negative ions at five points apart from each other by at least 50 cm near the center of the box using an air ion counter (part number ITC-201A) manufactured by Andes Denki, and by calculating an average concentration among the five points, and the concentrations of the positive and negative ions were adjusted to attain 3000/cm$^3$. The atmosphere in the box had the temperature of 25° C. and relative humidity of 60% RH. As shown in FIGS. 8A and 8B, respectively, it was considered that the emitted positive ions were H$_3$O$^+$ (H$_2$O)$_n$ (n is 0 or a natural number) and negative ions were O$_2^-$ (H$_2$O)$_m$ (m is 0 or a natural number), and that these positive and negative ions generate hydrogen peroxide H$_2$O$_2$, hydrogen dioxide HO$_2$ or hydroxy radical .OH by the chemical reactions (1) and (2) described above.

The spatial average concentration of positive and negative ions in the present invention refers to an average concentration in a whole space of a certain volume. This can be measured by measuring concentrations of positive and negative ions at five points apart from each other by at least 50 cm near the center of a room where the air stays appropriately, using an ion counter (for example, air ion counter (part number ITC-201A) manufactured by Andes Denki), and by calculating an average concentration among the five points.

Then, ion generating device 1021 and blower 1033 were stopped. Thereafter, an article 1032 carrying mite dust (2 g) was placed in box 1030, and ion generating device 1021 and blower 1033 were operated again, under the same condition as described above.

Thereafter, mite dust 1031 was diffused (scattered and caused to float) by flapping the article 1032 through a window 1034, using a diffuser 1035. The article 1032 may be a futon, blanket, carpet, tatami, pillow, cushion, pad or the like. In the present invention, a cushion was used. As the diffuser 1035, a flapper, a duster or a broom may be used. In the present example, a flapper was used. As for the diffusing operation, the article 1032 may be flapped, shaken or dropped down. In the present example, using a flapper as diffuser 1035, the cushion as article 1032 was flapped hard 20 times in 5 minutes.

Then, after flapping the cushion, an air suction pump 1037 mounted at an upper portion of box 1030 was operated, and the dust in box 1030 was sucked and recovered for 30 minutes, using a recovery filter 1036.

After 30 minutes, air suction pump 1037 was stopped and, again, using a flapper as diffuser 1035, the cushion as article 1032 was flapped hard 20 times in 5 minutes. Then, air suction pump 1037 was again operated, and the dust in box 1030 was sucked and recovered for 30 minutes, using a recovery filter 1036.

The amount of dust collected by recovery filter 1036 by two times of suction and collection described above was 0.7 mg.

For the operations described above, ion generating device 1021 was operated so as to cause reaction of positive and negative ions against mite dust (the mite dust processed in this manner will be referred to as ion-processed mite dust, and extraction therefrom will be referred to as ion-processed mite antigenic substance). For comparison, mite dust was recovered in the same manner as described above, except that ion generating device 1021 was not operated (the sample for comparison will be referred to as unprocessed mite dust, and extraction therefrom will be referred to as unprocessed mite antigenic substance).

Figure 17:
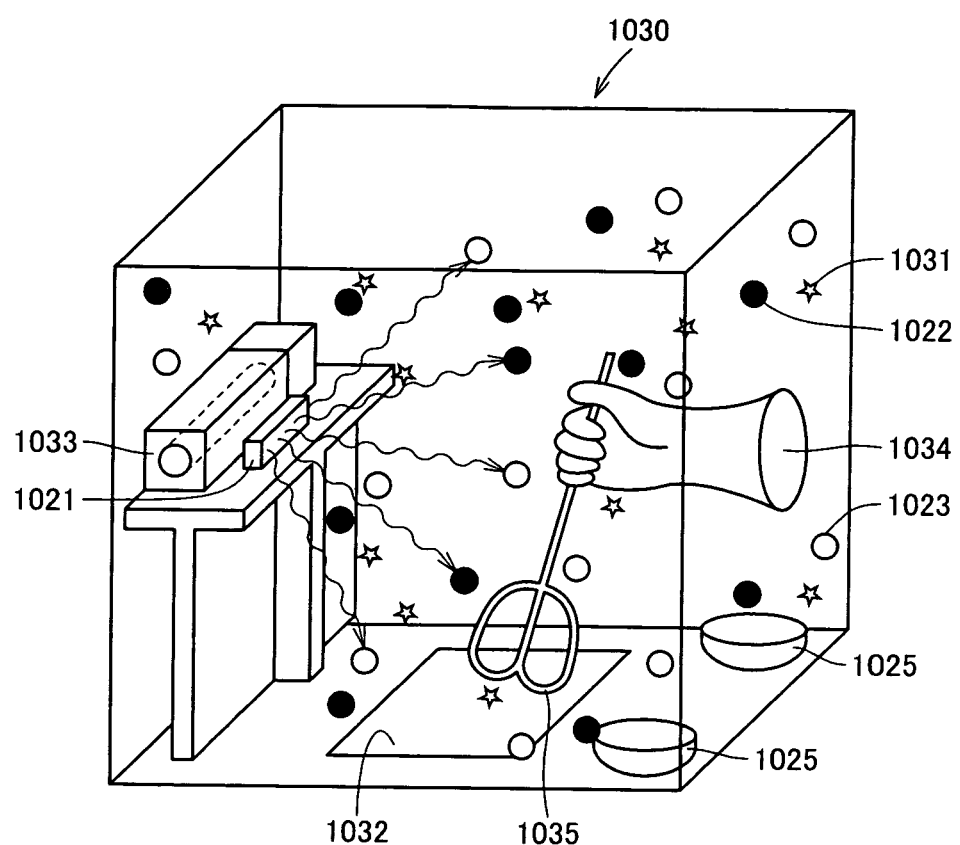
FIG. 17 is a schematic diagram showing an apparatus for executing the method of deactivating antigenic substance, including a blower and a recovery vessel.

For such operation, various apparatuses other than the apparatus shown in FIG. 16 described above may be used. For example, in place of air suction pump 1037 and recovery filter 1036 of FIG. 16, a recovery vessel 1025 may be placed to collect dust that falls naturally, as shown in FIG. 17 (in which the same reference characters as FIG. 16 denote the same or corresponding portions).

<Evaluation by ELIZA Inhibition Method>

For quantitative evaluation of reactivity between ion-processed and unprocessed mite antigenic substances and serum IgE of mite allergy patients, ELIZA inhibition (enzyme-liked immunosorbent assay inhibition) method was used.

Specifically, mite antigenic substance was extracted from the diffused and recovered mite dust, put in a centrifugal separator (Centriprep YM-10), and subjected to centrifugal condensation at 2500 rpm. Further, the condensation was put in a centrifugal separator (ULTRA FLEE-MC) and subjected to centrifugal condensation at 7000 rpm. Condensed ion-processed mite antigenic substance and condensed unprocessed mite antigenic substance were 5-times diluted from protein concentration of 7.66 μg/ml for 11 times. The diluted antigenic substances, 50 μl each, were mixed with 50 μl of 10-times diluted serum IgE of each patient, and pre-incubated overnight at 4° C.

Specifically, using a 96-well plate for ELISA, 50 μl of mite antigenic substance (not even sprayed) diluted to 1 μg/ml with bicarbonate buffer solution was applied to a well, and left still for 2 hours. The plate was washed three times with washing buffer solution, and then, 300 μl of blocking buffer solution was applied and left still overnight at 4° C.

After left still overnight, the plate was washed four times, and pre-incubated samples were applied, 50 μl per well, and left still for 4 hours. The plate was washed five times, and biotin-labeled anti-human IgE diluted 1000 times with (3% of skim milk+1% of BSA)/PBST was applied, 50 μl per well, and left still for 2.5 hours.

After left still, the plate was washed three times, 50 μl of alkali phosphatase labeled streptavidin diluted 1000 times with (3% of skim milk+1% of BSA)/PBST was applied, and left still for 1.5 hours at a room temperature. The plate was washed four times, Attophos (trademark) substrate buffer was applied, 50 μl per well, and left until colored, with light shielded. Fluorescent intensity was measured using a spectrophotometer (Cyto (trademark) FluorII). The reagents used were the same as those listed above, unless specified differently.

Reactivity (binding characteristic) to the serum IgE antibody of mite allergy patients, where ion generating device was not operated (that is, reactivity to unprocessed mite antigenic substance) and where the device was operated to attain spatial average concentration of 3,000/cm$^3$ for each of positive and negative ions (that is, reactivity to ion-processed mite antigenic substance) was studied. The results are as shown in FIG. 18.

Figure 18:
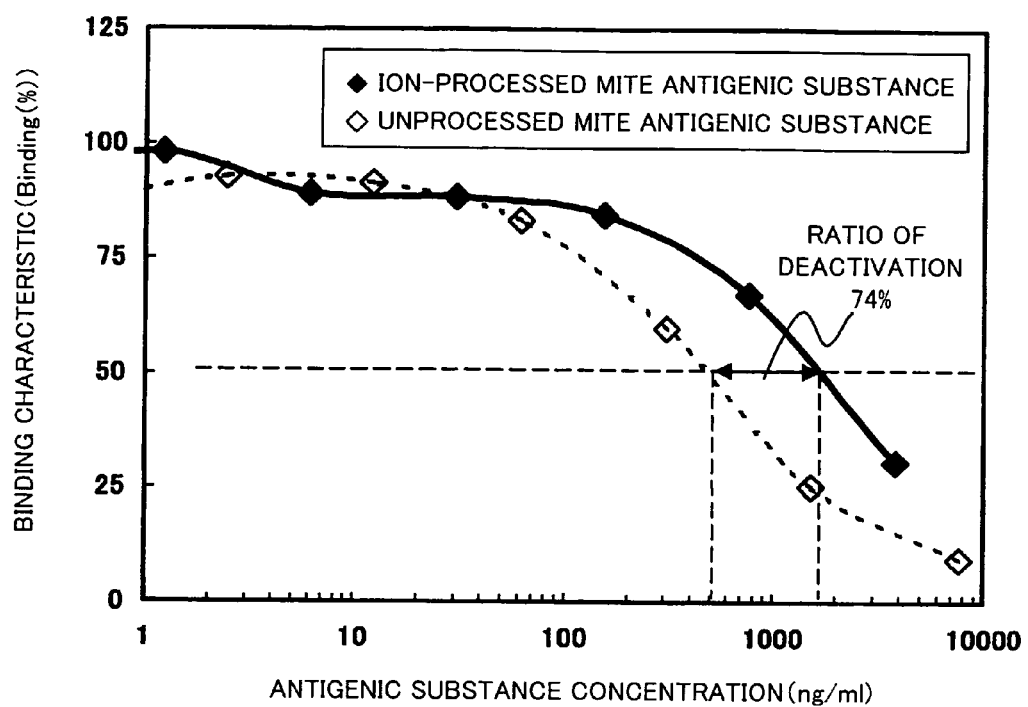
FIG. 18 represents relation of allergic reaction between the antigenic substance and the serum IgE antibody of mite allergy patients, when the mite dust was ion-processed and unprocessed, by ELISA inhibition method, with the spatial average concentration of positive and negative ions of 3000/$cm^3$ each.

As shown in FIG. 18, the amount of mite antigenic substance necessary for 50% inhibition (to lower reactivity of mite antigenic substance to serum IgE antibody to 50%) was 500 ng/ml in the case of unprocessed mite antigenic substance, while the necessary amount for 50% inhibition was 1900 ng/ml in the case of ion-processed mite antigenic substance, and therefore, the ratio of deactivation was confirmed to be 74%. Here, the ratio of deactivation was calculated in accordance with an equation similar to equation (1) above.

In this manner, it was confirmed that the positive and negative ions act directly on the antigenic substance and, in addition, act on the mite dust containing the antigenic substance. Further, the effect was confirmed that when spatial average concentration of positive and negative ions each attain 3000/cm$^3$, the antigenic substance could be deactivated.

Example 5

In the present example, functions of the positive and negative ions on mite dust were confirmed in the similar manner as in Example 4, except that, different from Example 4, the spatial average concentration of positive and negative ions each were set to 10,000/cm$^3$ (by setting the peak-to-peak voltage between electrodes of ion generating device 1021 to 100V and setting fan flow rate of blower 1033 to 8 m$^3$/min). The results are as shown in FIG. 19.

Figure 19:
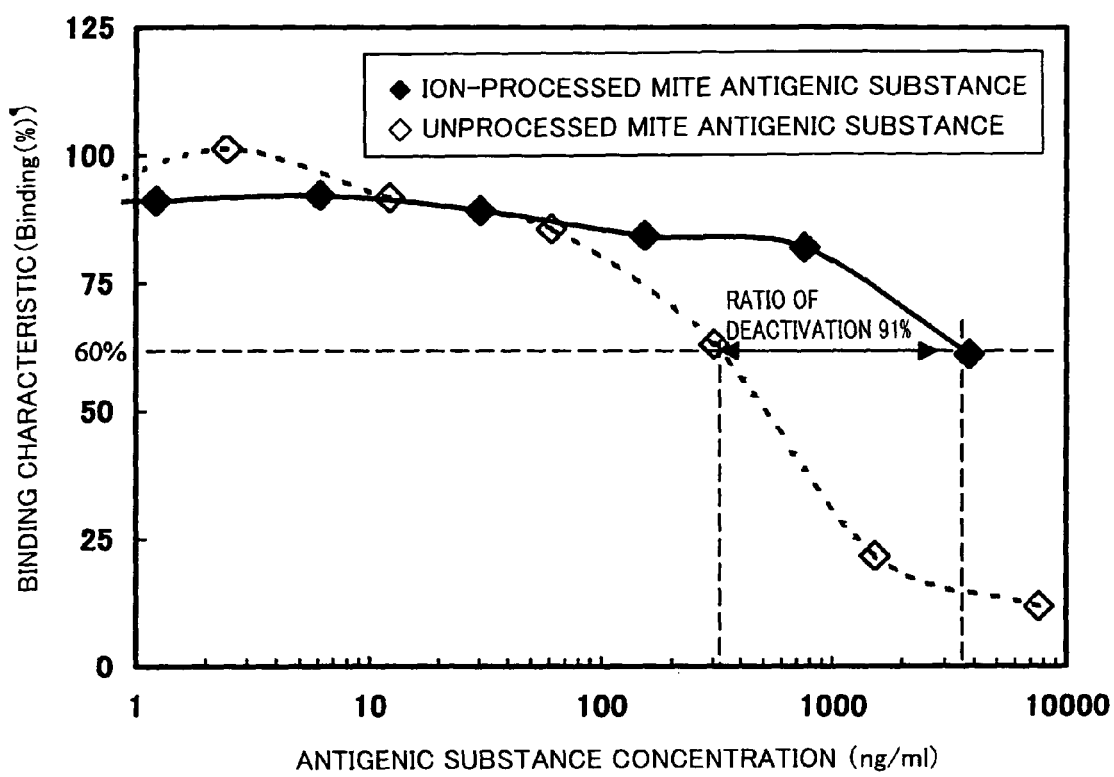
FIG. 19 represents relation of allergic reaction between the antigenic substance and the serum IgE antibody of mite allergy patients, when the mite dust was ion-processed and unprocessed, by ELISA inhibition method, with the spatial average concentration of positive and negative ions of 10000/$cm^3$ each.

As shown in FIG. 19, the amount of mite antigenic substance necessary for 60% inhibition (to lower reactivity of mite antigenic substance to serum IgE antibody to 60%) was 345 ng/ml in the case of unprocessed mite antigenic substance, while the necessary amount for 60% inhibition was 3823 ng/ml in the case of ion-processed mite antigenic substance, and therefore, the ratio of deactivation was confirmed to be 91%. Here, the ratio of deactivation was calculated in accordance with equation (1) as above.

In this manner, it was confirmed that when spatial average concentration of positive and negative ions each attain 10,000/cm$^3$, the antigenic substance could be deactivated.

When FIGS. 18 and 19 are compared, though there is a difference of 50% inhibition and 60% inhibition, it can be understood from FIG. 18 that the higher the spatial average concentration, the higher the ratio of deactivation, as the ratio of deactivation for 50% inhibition and 60% inhibition can be regarded substantially the same, in accordance with FIG. 18.

As described above, by the method of the present invention, the antigenic substance can effectively be deactivated by the reaction with positive and negative ions. Thus, it is expected that the method can be used for effectively suppressing various allergic diseases such as hey fever and mite allergy, caused by such antigenic substances.

Further, by using the method or apparatus of the present invention inside or outside an air conditioning apparatus, it becomes possible to feed air with antigenic substance deactivated, or to directly deactivate the air-borne antigenic substance by ion emission described above.

In each of the above-described examples, description has been made mainly focusing on allergens included in pollen and mite. It is noted, however, that the air purifier in accordance with the present invention is also considered effective to allergens included in mold and the like, other than pollen and mite.

Although the present invention has been described and illustrated in detail, it is clearly understood that the same is by way of illustration and example only and is not to be taken by way of limitation, the spirit and scope of the present invention being limited only by the terms of the appended claims.

INDUSTRIAL APPLICABILITY

As described, by using the method and apparatus for evaluating performance of an activation gas deactivating an antigenic substance in accordance with the present invention, the performance of various activation gases deactivating various antigenic substances can be evaluated accurately in a simple manner.

The invention claimed is:

1. A method of evaluating performance of an activation gas containing both positive and negative ions in deactivating an antigenic substance floating in the air by measuring binding activity of a processed antigenic substance with an antibody, comprising the steps of:

causing the antigenic substance floating in the air and said activation gas to react with each other, to obtain a processed antigenic substance;

causing an antibody against said antigenic substance to react with said processed antigenic substance, by intradermal test or conjectival test or intradermal test and conjectival test on an animal other than a human having a cell producing said antibody against said antigenic substance, to measure binding activity of said processed antigenic substance with said antibody; and comparing the measured binding activity of the processed antigenic substance with the binding activity of the same amount of unprocessed antigenic substance, wherein reduced binding activity in the processed antigenic substance is indicative of an effect of said activation gas deactivating the antigenic substance.

2. A method of evaluating performance of an activation gas containing both positive and negative ions in deactivating an antigenic substance floating in the air by comparing binding activity of said antigenic substance with an antibody to binding activity of a processed antigenic substance with said antibody, comprising the steps of causing the antigenic substance floating in the air and said activation gas to react with each other, to obtain a processed antigenic substance;

causing an antibody against said antigenic substance to react with said processed antigenic substance, by intradermal test or conjectival test or intradermal test and conjectival test on an animal other than a human having a cell producing said antibody against said antigenic substance, to measure binding activity of said processed antigenic substance with said antibody; and comparing the binding activity of said processed antigenic substance to binding activity of said antigenic substance with said antibody, wherein reduced binding activity in the processed antigenic substance is indicative of an effect of said activation gas deactivating the antigenic substance.

3. The method of evaluating performance of an activation gas deactivating an antigenic substance according to claim 1, wherein said step of causing reaction includes the steps of: dispersing a solution containing said antigenic substance in a container, causing said dispersed solution containing said antigenic substance to float in the air, and introducing said activation gas into said container.

4. The method of evaluating performance of an activation gas deactivating an antigenic substance according to claim 1, wherein said step of obtaining said processed antigenic substance includes the step of causing said antigenic substance to float in the air, by vibrating, or shocking, or vibrating and shocking said antigenic substance.

5. The method of evaluating performance of an activation gas deactivating an antigenic substance according to claim 4, wherein said step of causing floating includes the steps of: placing said antigenic substance on a flexible sample table; and vibrating, or shocking, or vibrating and shocking said sample table.

6. The method of evaluating performance of an activation gas deactivating an antigenic substance according to claim 4, wherein said step of causing floating includes the steps of:

placing said antigenic substance on a flexible sample table formed of at least one selected from the group consisting of a futon, a blanket, a cushion, a pillow, a mat, a sponge, cloth, paper and styrene foam; and vibrating, or shocking, or vibrating and shocking said sample table by flapping, or shaking, or flapping and shaking said sample table.

7. The method of evaluating performance of an activation gas deactivating an antigenic substance according to claim 1, wherein said step of obtaining said processed antigenic substance includes the step of causing at least one selected from the group consisting of an antigenic substance included in cedar pollen and/or mite dust, cedar pollen and mite dust to react with the activation gas, to obtain the processed antigenic substance.

* * * * *